United States Patent
Pelleg et al.

(10) Patent No.: US 11,440,935 B2
(45) Date of Patent: Sep. 13, 2022

(54) 3",5"-DIMETHOXYBENZOYL-3'-AMINO-3'-DEOXY ADENOSINE-5'-TRIPHOSPHATES AND PHARMACEUTICAL USES THEREOF

(71) Applicant: Danmir Therapeutics, LLC, Haverford, PA (US)

(72) Inventors: Amir Pelleg, Haverford, PA (US); Anu Mahadevan, Nestford, MA (US); Jie Li, Winchester, MA (US); Cynthia Morency, Andover, MA (US)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 16/981,242

(22) PCT Filed: Mar. 14, 2019

(86) PCT No.: PCT/US2019/022213
§ 371 (c)(1),
(2) Date: Sep. 15, 2020

(87) PCT Pub. No.: WO2019/178331
PCT Pub. Date: Sep. 19, 2019

(65) Prior Publication Data
US 2021/0054015 A1 Feb. 25, 2021

Related U.S. Application Data

(60) Provisional application No. 62/643,199, filed on Mar. 15, 2018.

(51) Int. Cl.
*C07H 19/20* (2006.01)
*A61P 11/08* (2006.01)
(Continued)

(52) U.S. Cl.
CPC .......... *C07H 19/20* (2013.01); *A61K 31/706* (2013.01); *A61P 11/08* (2018.01); *A61P 11/14* (2018.01);
(Continued)

(58) Field of Classification Search
CPC . C07H 19/20; C07H 1/04; A61P 11/08; A61P 11/14
See application file for complete search history.

(56) References Cited

U.S. PATENT DOCUMENTS

| | | | |
|---|---|---|---|
| 5,620,676 A | 4/1997 | Jacobson et al. | |
| 6,693,136 B1* | 2/2004 | Lee | C07C 311/21 514/437 |

(Continued)

OTHER PUBLICATIONS

Abdulqawi et al., "P2X3 receptor antagonist (AF-219) in refractory chronic cough: a randomised, double-blind, placebo-controlled phase 2 study" The Lancet vol. 385 pp. 1198-1205 http://dx.doi.org/10.1016/S0140-6736(14)61255-1 (Year: 2014).*

(Continued)

*Primary Examiner* — Eric Olson
(74) *Attorney, Agent, or Firm* — Faegre Drinker Biddle & Reath LLP

(57) ABSTRACT

Provided are compounds compound according to Formula (I), or a pharmaceutically acceptable salt, solvate, coordination complex or prodrug thereof: wherein, $R^1$ and $R^2$ are independently selected from $(C_1-C_6)$ alkyl. The compounds have P2X3 receptor or P2X2/3 receptor antagonist activity and are useful for the treatment of diseases and disorders characterized by activation of those receptors.

(Continued)

[1] 3",5"-dimethoxybenzoyl-3'-amino-3'-deoxyadenosine-5'-triphosphate

(52) U.S. Cl.
CPC ............... *A61P 29/00* (2018.01); *A61P 31/10* (2018.01); *C07H 1/04* (2013.01)

(56) References Cited

U.S. PATENT DOCUMENTS

| | | | |
|---|---|---|---|
| 9,284,279 | B2 | 3/2016 | Ford et al. |
| 2004/0019042 | A1 | 1/2004 | Lee et al. |
| 2010/0222294 | A1 | 9/2010 | Pelleg |
| 2015/0119352 | A1 | 4/2015 | Miller et al. |

OTHER PUBLICATIONS

Adraensen et al., "Sensory input to the central nervous systemfromthe lungs and airways: A prominent role for purinergic signaling via P2X2/3 receptors" Autonomic Neuroscience: Basic and Clinical vol. 191 pp. 39-47 http://dx.doi.org/10.1016/j.autneu.2015.04.006 (Year: 2015).*

Bae et al., "Synthesis and Structure—Activity Relationship Studies of Benzimidazole-4,7-dione-Based P2X3 Receptor Antagonists as Novel Anti-Nociceptive Agents" Molecules vol. 27 https://doi.org/10.3390/molecules27041337 (Year: 2022).*

Koles et al., "Purine Ionotropic (P2X) Receptors" Current Pharmaceutical Design vol. 13 pp. 2368-2384 (Year: 2007).*

International Preliminary Report on Patentability for PCT/US2019/022213 dated Jun. 3, 2019.

North, R. Alan, et al., "P2X Receptors as Drug Targets", Molecular Pharmacology, vol. 83, No. 4, (2013), pp. 759-769.

* cited by examiner

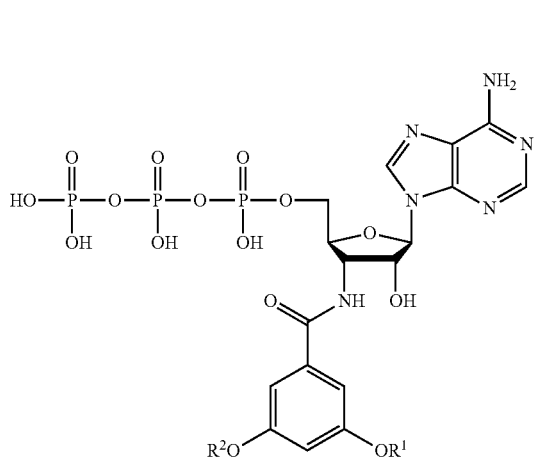

(I)

19 Claims, 10 Drawing Sheets

(51) Int. Cl.

| | |
|---|---|
| *A61P 11/14* | (2006.01) |
| *A61P 29/00* | (2006.01) |
| *C07H 1/04* | (2006.01) |
| *A61K 31/706* | (2006.01) |
| *A61P 31/10* | (2006.01) |

[1] 3",5"-dimethoxybenzoyl-3'-amino-3'-deoxyadenosine-5'-triphosphate

3",5"-dimethoxybenzoyl-3'-amino-3'-deoxyadenosine-5'-triphosphate (μM)

Fig. 11

3",5"-DIMETHOXYBENZOYL-3'-AMINO-3'-DEOXY ADENOSINE-5'-TRIPHOSPHATES AND PHARMACEUTICAL USES THEREOF

CROSS-REFERENCE TO RELATED APPLICATIONS

This application is a national stage application (under 35 U.S.C. § 371) of PCT/US2019/022213, filed Mar. 14, 2019, which claims benefit of U.S. Application No. 62/643,199, filed Mar. 15, 2018, both of which are incorporated herein by reference in their entirety.

FIELD OF THE INVENTION

The invention relates to compounds, methods for their preparation, and compositions including them. The invention further provides methods for the treatment of disorders treatable with antagonists of P2-purinergic receptors (P2R) in particular P2X3 and P2X2/3.

BACKGROUND OF THE INVENTION

Extracellular adenosine 5'-triphosphate (ATP) is an autocrine and paracrine mediator; the effects of extracellular ATP are mediated by cell-surface P2R, which are divided into two families: (1) trans-cell membrane cationic channels (P2XR); and (2) seven trans-membrane domain G protein-coupled receptors (P2YR). Six homomeric P2X receptors (P2X1, P2X2, P2X3, P2X4, P2X5, and P2X7) and three heteromeric receptors (P2X2/3, P2X4/6 and P2X1/5) have been identified heretofore.

P2R are abandoned in the lungs (Burnstock et al., *Pharmacol Rev*, 64, 834-68; Brouns et al. *Am J Respir Cell Mol Biol.* 2000; 23(1):52-61.). In 1996, Pelleg et al. have shown for the first time that extracellular ATP is a potent activator of the canine pulmonary vagal sensory nerve fibers (C fibers) in vivo (Pelleg and Hurt, 1996; *J Physiol* (*Lond*) 1; 490 (Pt 1):265-75). This action is mediated by bimodal P2X receptors (P2XR), which respond to both mechanical (stretch) and chemical (e.g., capsaicin) stimuli (Pelleg and Hurt, 1996; *J Physiol* (*Lond*) 1; 490 (Pt 1):265-75). At that year, Pellegrino et al. have shown that aerosolized ATP is a potent bronchoconstrictor in human subjects (Pellegrino et al., 1996; *J Appl Physiol* 81(2):964-75). Similarly, intravenous ATP caused bronchoconstriction in the canine lungs (Katchanov et al., 1998; *Drug Devel Res* 45:342-349). Based on these and other early studies, Pelleg et al. hypothesized in 2002 for the first time that extracellular ATP plays an important mechanistic role in pulmonary pathophysiology in general and chronic obstructive disease in (Pelleg & Schulman, *Am J Therap* 2002; 9(5):454-64). Since then, numerous studies have generated voluminous data in support of this hypothesis (Pelleg et al., *Chest.* 2016; 150(4): 908-915). Importantly, multiple studies using various murine models have confirmed that stimulation of vagal sensory nerve endings in the lungs via the activation of P2XR (Driessen et al., *Respir Physiol Neurobiol.* 2016; 226:115-120; McQueen et al., *J Physiol.* 1998; 507(pt 3):843-855; Kollarik et al., *J Physiol.* 2003; 551(pt 3):869-879).

Regarding the effects of ATP on vagal sensory nerve terminals in the lungs, Pelleg et al. have subsequently shown that in addition to C fibers, ATP stimulates also the fast conducting Aδ fibers, the stimulation of both types was mediated the activation of P2X2/3R (Pelleg and Undem, *Clin Immunol.* 2005; 115: S59-S60). The stimulation of C fibers and Aδ fibers should also trigger cough as both C and Aδ fibers mediate cough.

ATP binding to P2XR is associated with certain disease etiologies including respiratory diseases. Increased amounts of extracellular ATP are found in the lungs of patients with chronic obstructive pulmonary disease (COPD), and ATP affects multiple cell types in the lungs, resulting in increased inflammation, induction of bronchoconstriction, and cough (Pelleg et al., *Chest.* 2016; 150(4):908-915).

Receptors containing P2X3 subunits (homotrimeric P2X3 and heterotrimeric P2X2/3 receptors) play a critical role in mediating the primary sensory effects of ATP. See, e.g., Ford, *Purinergic Signalling* (2012) 8(Suppl 1):3-26. P2X3R and P2X2/3R are predominantly localized on small-to-medium diameter C- and Aδ-fibers of sensory neurons within the dorsal root ganglion (DRG) and cranial sensory ganglia, and on their peripheral nerve terminals in receptive fields in various tissues including the skin and joints. ATP enhances the cough reflex, an effect that is not abolished by C-fiber desensitization, and capsaicin-induced coughs are inhibited by the desensitization of C fibers. Aerosolized ATP acts as a potent tussigenic agent in patients with COPD and asthma (Bosuglu et al., *Chest.* 2005; 128(4):1905-1909; Bosuglu et al., *Chest.* 2015; 148(2):430-435). In accordance with these findings in animal models and human patients, results of a recent study have implicated extracellular ATP and the P2X2/3R in the mechanism of cough in patients with chronic idiopathic cough. Specifically, in a study aimed at investigating the efficacy of a first-in-class oral P2X3R antagonist (AF-219) at reducing cough frequency in patients with refractory chronic cough, cough frequency was reduced by 75% when patients were allocated to receive AF-219 compared with placebo (Abdulqawi et al., *Lancet.* 2015; 385(9974):1198-1205). It has also been shown that the activation of TRPV4 receptors or application of hypoosmotic solution led to the stimulation of the guinea pig airway-specific primary nodose ganglion cell afferents (Aδ fibers [not C fibers]) and coughing. The effects of TRPV4 receptor activation were markedly attenuated by either a TRPV4R antagonist or the selective P2X3 receptor antagonist, AF-353, indicating that endogenous release of ATP and the activation of the P2X3 receptor are prerequisites for the TRPV4R-mediated effects of hypoosmotic action on the airways (Szallasi et al., *Br J Pharmacol.* 1999; 128(2):428-434). However, XEN-D0501, a novel TRPV1 antagonist, did not reduce cough in patients with refractory cough (Belvisi M G, et al., *Am J Respir Crit Care Med.* 2017; 196(10):1255-1263)

These studies clearly indicate that ATP is released into the extracellular space from the airways' epithelial and smooth muscle cells under physiologic and pathophysiologic conditions, and plays an important role in pulmonary inflammation in general and COPD, asthma, and chronic cough in particular (Pelleg et al., *Chest.* 2016; 150(4):908-915). This role is manifested, among other aspects, in airway hypersensitivity, modulation of immune cell functions, neutrally mediated bronchoconstriction, and tussigenic effects (Id.).

Selective antagonists of P2R subtypes that would inhibit specific signal transduction pathways activated by these receptors, particularly the receptors P2X3 and P2X2/3, are candidates for the management of respiratory diseases, including asthma, COPD, and cough, including chronic cough, in particular. As indicated above, clinical trials demonstrated that AF-219, a P2X3 receptor antagonist, was effective in preventing cough in patients with chronic cough that was refractory to current therapies (Abdulqawi et al., supra). For further examples of P2X3 and/or P2X2/3 receptor antagonists for the treatment of diseases driven or mediated by P2X3 and/or P2X2/3 receptor activation, and cough-induced respiratory disease in particular, see U.S. Pat. No. 9,284,279.

In addition to the treatment of respiratory disorders, P2X3R and/or P2X2/3R antagonists have been demonstrated useful for the treatment of various forms of pain (Jarvis, *Expert Opin Ther Targets.* 2003; 7(4):513-22). P2 XR antagonists have been shown to be analgesic in animal models (Driessen and Starke, *Naunyn Schmiedebergs Arch Pharmacol* 350:618-625 (1994)). ATP, through its actions as an excitatory neurotransmitter, plays a prominent role in the initiation and maintenance of chronic pain states. ATP-induced activation of P2 XR on dorsal root ganglion nerve terminals in the spinal cord stimulates the release of glutamate, a key neurotransmitter involved in nociceptive signaling. Thus, ATP released from damaged cells can evoke pain by activating P2X3 R and/or P2X2/3 R localized on nociceptive nerve endings of sensory nerves. For a review on the use of P2XR antagonists in management of pain, see Gum, et al., *Purinergic Signalling* (2012) 8(Suppl 1): 41-56. For a review of antagonism of P2X3-containing receptors (P2X3R and P2X2/3R) for the treatment of chronic pain and afferent sensitization, see Ford, *Purinergic Signal.* 8 (Suppl. 1) 3-26 (2012). Also see, US Pat. Pub. 2004/0019042 for examples of compounds determined to be P2X3R and P2X2/3R antagonists based on their ability to inhibit increases in cytosolic $Ca^{2+}$ concentration elicited by the P2X receptor agonist α,β-methyleneATP, a selective P2XR agonist, as a percentage of the maximal α,β-methyleneATP response in the absence of test antagonist. Also described in US Pat. Pub. 2004/0019042 is a correlation of such in vitro P2X3R and P2X2/3R antagonism results with in vivo antinociceptive effect.

P2X3R and/or P2X2/3R antagonists have further been described as useful for the treatment of various forms of disorders of the bladder, including bladder overactivity, urinary incontinence and interstitial cystitis. The latter, also known as painful bladder syndrome, is a chronic condition causing bladder pressure, bladder pain and sometimes pelvic pain. For examples of P2X3R and/or P2X2/3R antagonist compounds described as being useful for treatment of such bladder disorders, see, e.g., US Pat. Pub. 2004/0019042.

For a recent review of P2X3R and/or P2X2/3R antagonists and corresponding treatment indications, see Bölcskei and Farkas, *Pharm. Pat. Analyst,* 3(1):1-12 (2014).

There is a critical need for additional P2X3R and/or P2X2/3R antagonists for the treatment of multiple disorders, in which P2X3R and/or P2X2/3R activation plays a mechanistic role.

SUMMARY OF THE INVENTION

In one aspect, a compound according to Formula (I), or a pharmaceutically acceptable salt, solvate, coordination complex or prodrug thereof, is provided:

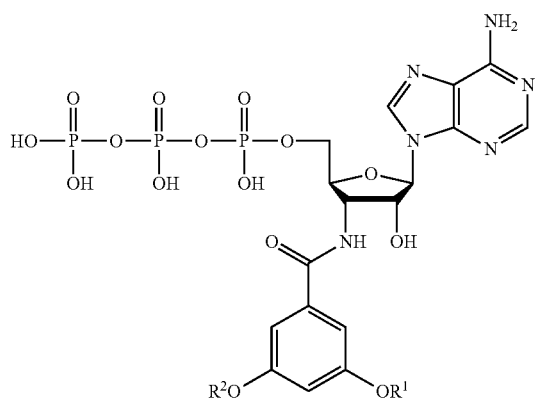

wherein:

$R^1$ and $R^2$ are independently selected from $(C_1$-$C_6)$ alkyl.

In certain embodiments, $R^1$ and $R^2$ are preferably independently selected from $(C_1$-$C_3)$ alkyl. Most preferably, $R^1$ and $R^2$ are methyl.

In a particularly preferred embodiment, the compound is a sodium salt of the compound of formula (I) depicted by the following formula:

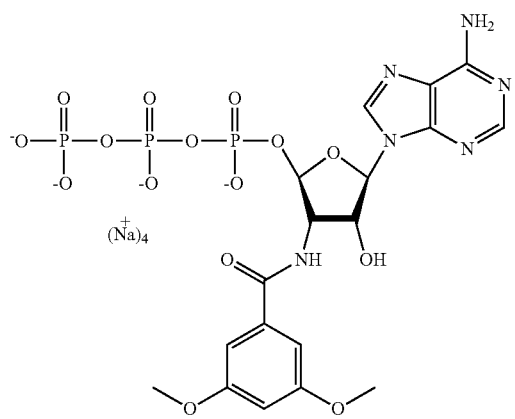

In another aspect, provided are processes for preparing compounds according to Formula (I). The process comprises:

(a) reacting the compound 1

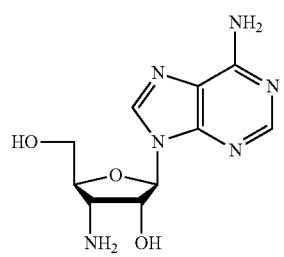

with a compound of Formula (IIa)

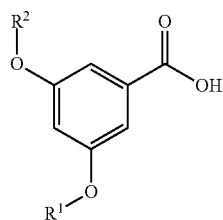

to form a compound according to Formula (III);

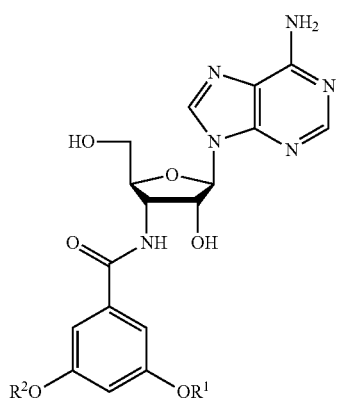

(b) 5-phosphorylating the compound according to Formula (III) to provide a compound according to Formula (I). The compound of Formula (I) may be isolated as a salt, solvate, or coordination complex, or may be converted to a salt, solvate or coordination complex following isolation.

In an intermediate step prior to the reaction of the compound of formula I with the compound of Formula (IIa), the compound 1 may optionally be protected with one or more silyl groups, for example tert-butyldimethylsilyl groups. An example of a capped compound of formula 1 which may be reacted with the compound of Formula (IIa) is depicted below:

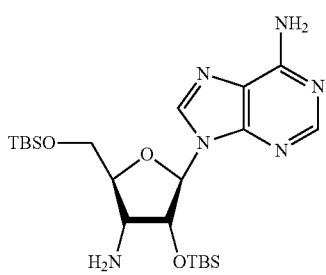

In this formula, TBS is tert-butyl(dimethyl)silyl.

In another aspect, provided are pharmaceutical compositions comprising a pharmaceutically acceptable carrier, and a compound according to Formula (I), or a pharmaceutically acceptable salt, solvate, coordination complex or prodrug thereof.

According to another embodiment of the invention, a method for treating a respiratory disease in a subject in need of such treatment is provided, wherein the respiratory disease is meditated by an antagonist of a P2X3R or P2X2/3R antagonist. The method comprises administering to the subject in need of such treatment a therapeutically effective amount of a compound of Formula (I) or a pharmaceutically acceptable salt, solvate, coordination complex or prodrug thereof.

In some embodiments, the respiratory disorder is chronic obstructive pulmonary disease (COPD), asthma, emphysema, chronic cough, idiopathic pulmonary fibrosis (IPF), or combinations thereof.

According to another embodiment of the invention, a method for treating or controlling pain in a subject in need of such treatment is provided. The method comprises administering the subject in need thereof a therapeutically effective amount of a compound of Formula (I) or a pharmaceutically acceptable salt, solvate, coordination complex or prodrug thereof.

In some embodiments, the pain is nociceptive pain.

According to another embodiment of the invention, a method for treating a disorder of the bladder in a subject in need of such treatment is provided. The method comprises administering to the subject in need thereof a therapeutically effective amount of a compound of Formula (I) or a pharmaceutically acceptable salt, solvate, coordination complex or prodrug hereof.

In some embodiments, the disorder of the bladder is bladder overactivity, urinary incontinence or interstitial cystitis.

The aforementioned disorders treatable with compounds of the invention comprise disorders that are characterized by activation of P2X3R and/or P2X2/3R. As shown below, compounds of the invention are antagonists of P2X3-containing receptors, that is antagonists of P2X3R and P2X2/3R.

Also provided is a compound of Formula (I), or pharmaceutically acceptable salt, solvate, coordination complex or prodrug thereof, for use in medicine.

Also provided is a compound of Formula (I), or pharmaceutically acceptable salt, solvate, coordination complex or prodrug thereof, for preparation of a medicament (i) for treating a respiratory disease, wherein the respiratory disease is meditated by a P2X3R or P2X2/3R antagonist; (ii) for treating or controlling pain; or (iii) for treating a disorder of the urinary bladder.

Also provided is a pharmaceutical composition comprising a compound of Formula (I), or pharmaceutically acceptable salt, solvate, coordination complex or prodrug thereof, and a pharmaceutically acceptable carrier.

Also provided is a compound of Formula (I), or pharmaceutically acceptable salt, solvate, coordination complex or prodrug thereof, for inhibiting activity of P2X3R and/or P2X2/3R.

Also provided is a compound of Formula (I), or pharmaceutically acceptable salt thereof for preparation of a medicament for treatment for treatment of a disorders characterized by pathological activation of P2X3R and/or P2X2/3R.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

Any open valence appearing on a carbon, oxygen or nitrogen atom in the structures herein indicates the presence of a hydrogen atom.

EXEMPLARY EMBODIMENTS

1. A compound according to Formula (I), or a pharmaceutically acceptable salt, solvate, coordination complex or prodrug thereof:

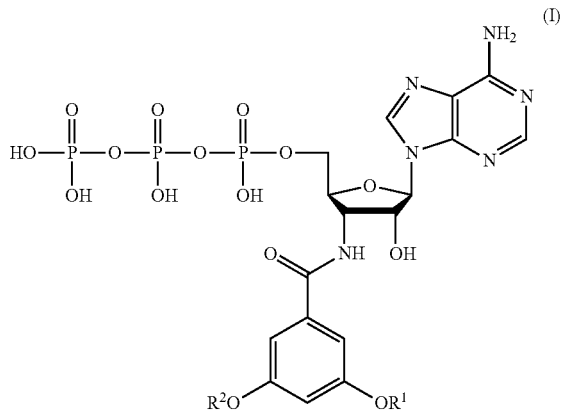

wherein:

$R^1$ and $R^2$ are independently selected from $(C_1-C_6)$ alkyl.

2. The compound according to embodiment I wherein $R^1$ and $R^2$ are methyl, or a pharmaceutically acceptable salt, solvate, coordination complex or prodrug thereof.

3. The compound according to embodiment I or 2, wherein the compound is a sodium salt of the following formula:

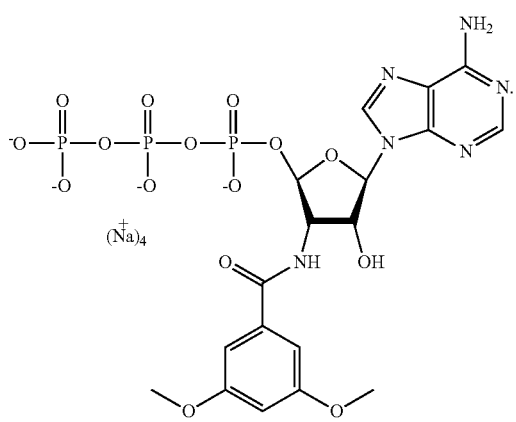

4. A pharmaceutical composition comprising a pharmaceutically acceptable carrier and a compound according to any of the above embodiments, or pharmaceutically acceptable salt, solvate, coordination complex or prodrug thereof.

5. A pharmaceutical composition comprising a pharmaceutically acceptable carrier and a compound according to any of the above embodiments, or pharmaceutically acceptable salt, solvate, coordination complex or prodrug thereof.

6. A method of treating respiratory disease meditated by an antagonist of a P2X3 or P2X2/3R antagonist comprising administering to the subject in need of such treatment a therapeutically effective amount of a compound according to any of the above embodiments, or pharmaceutically acceptable salt, solvate, coordination complex or prodrug thereof.

7. The method according to embodiment 5 wherein the respiratory disease is a cough related respiratory disease.

8. The method according to embodiment 5 or 6 wherein cough-related the respiratory disease is chronic obstructive pulmonary disorder (COPD), bronchospasm or asthma.

9. The method according to any of embodiments 6-8 wherein the respiratory disease is disease is sub-acute cough, chronic cough, treatment-resistant cough, idiopathic chronic cough, cough associated with upper respiratory infection, post-viral cough, iatrogenic cough, idiopathic pulmonary fibrosis or cough associated with smoking or a form of bronchitis.

10. The method according to any of embodiments 6 to 9, wherein $R^1$ and $R^2$ are methyl in the compound of Formula (I), or in the pharmaceutically acceptable salt, solvate, coordination complex or prodrug thereof.

11. A method of treating a disorder of the bladder comprising administering to a subject in need of such treatment a therapeutically effective amount of a compound according to any of embodiments 1 to 3, or pharmaceutically acceptable salt, solvate, coordination complex or prodrug thereof.

12. The method according to embodiment 11 wherein the disorder of the bladder is bladder overactivity or urinary incontinence.

13. The method according to embodiment 11 or 12 wherein the bladder overactivity comprises one or more of urinary urgency, urinary frequency, altered bladder capacity, micturition threshold, unstable bladder contractions, sphincteric spasticity, detrusor hyperreflexia and detrusor instability.

14. The method according to any of embodiments 11-13 where in the disorder of the bladder is interstitial cystitis.

15. The method according to any of embodiments 11 to 14, wherein $R^1$ and $R^2$ are methyl in the compound of Formula (I), or in the pharmaceutically acceptable salt, solvate, coordination complex or prodrug thereof.

16. A method of treating pain comprising administering to a subject in need of such treatment a therapeutically effective amount of a compound according to any of embodiments 1 to 3, or pharmaceutically acceptable salt, solvate, coordination complex or prodrug thereof.

17. The method according to embodiment 16 wherein the pain is nociceptive pain.

18. The method according to embodiment 16 or 17 wherein the pain is neuropathic pain.

19. The method according to embodiment 16 or 17, wherein $R^1$ and $R^2$ are methyl in the compound of Formula (I), or in the pharmaceutically acceptable salt, solvate, coordination complex or prodrug thereof.

20. A process for preparing a compound according to Formula (I),

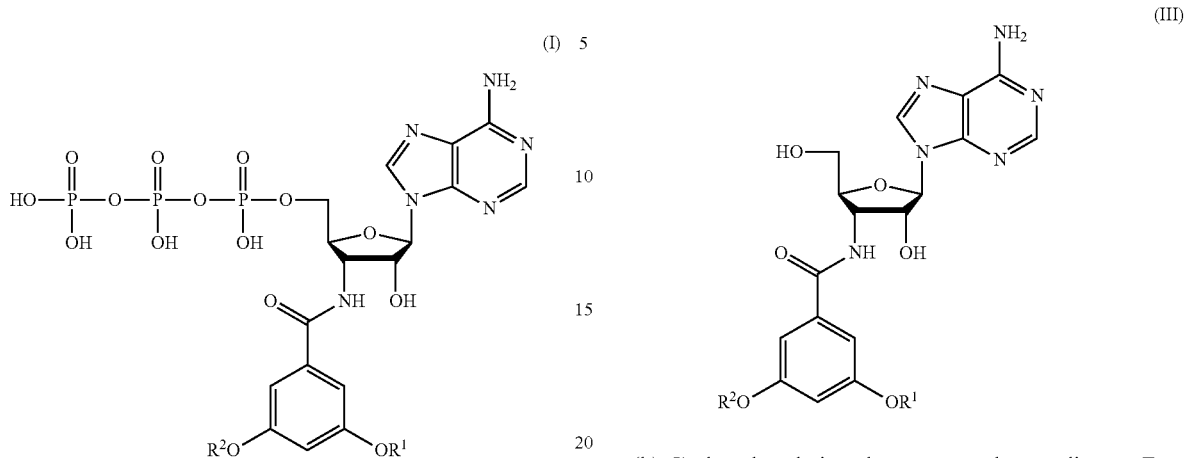

wherein:

R$^1$ and R$^2$ are independently selected from (C$_1$-C$_6$) alkyl;

the process comprising:

(a) reacting the compound 1

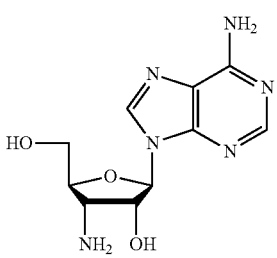

with a compound of Formula (IIa)

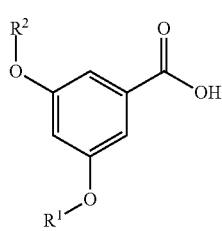

to form a compound according to Formula I;

(b) 5'-phosphorylating the compound according to Formula (II) to provide a compound according to Formula (I).

21. The process according to embodiment 20 wherein R$^1$ and R$^2$ are methyl.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for describing particular embodiments only and is not intended to be limiting.

The articles "a" and "an" are used herein to refer to one or to more than one (i.e., to at least one) of the grammatical object of the article. By way of example, "an element" means one element or more than one element. Thus, recitation of "a cell", for example, includes a plurality of the cells of the same type.

"About" as used herein when referring to a measurable value such as an amount, a temporal duration, and the like, is meant to encompass variations of +/−20% or +/−10%, more preferably +/−5%, even more preferably +/−1%, and still more preferably +/−0.1% from the specified value, as such variations are appropriate to perform the disclosed methods.

"Agonist" refers to a compound that enhances the activity of another compound or receptor site.

"Antagonist" refers to a compound that diminishes or prevents the action of another compound or receptor site.

The term "alkyl", by itself or as part of another substituent means, unless otherwise stated, a straight or branched chain hydrocarbyl having the designated number of carbon atoms (i.e., C$_1$-C$_6$ means one to six carbons). Examples include: methyl, ethyl, propyl, isopropyl, butyl, isobutyl, tert-butyl, pentyl, neopentyl, and hexyl. Most preferred is (C$_1$-C$_3$) alkyl, particularly methyl and ethyl.

The term "alkoxy" employed alone or in combination with other terms means, unless otherwise stated, an alkyl group, as defined above, connected to the rest of the molecule via an oxygen atom, such as, for example, methoxy, ethoxy, 1-propoxy, 2-propoxy (isopropoxy) and the higher homologs and isomers. The alkyl portion of the alkoxy group can have a designated number of carbon atoms as defined for alkyl groups above.

"Disorder of the bladder" means a pathologic change in the bladder. Examples of disorders of the bladder include, but are not limited to overactive bladder, urinary incontinence, interstitial cystitis, and the like. "Overactive bladder" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

An "effective amount" or "therapeutically effective amount" as used herein, means an amount of compound, when administered to a patient provides a therapeutic benefit in alleviating one or more manifestations of the disease. It is understood, however, that the full therapeutic effect does not necessarily occur by administration of one dose, and may occur only after administration of a series of doses. Thus, an effective amount may be administered in one or more administrations.

As used herein, "individual" or "subject" (as in the subject of the treatment) means both mammals and non-mammals. Mammals include, for example, humans; non-human primates, e.g. apes and monkeys; cattle; horses; sheep; and goats. Non-mammals include, for example, fish and birds. The individual is, in one embodiment, a human being.

"Modulator" means a molecule that interacts with a target. The interactions include, but are not limited to, agonist, antagonist, and the like, as defined herein.

"Pharmaceutically acceptable" when referring to a carrier for an active compound, or to a salt, solvate, coordination complex or prodrug of an active compound, means that the carrier, salt, solvate, coordination complex or prodrug does not significantly abrogate the biological activity, a pharmacological activity and/or other properties of the active agent when so constituted and administered to a patient.

"Respiratory disorder" or "respiratory disease" refers to disorders of the respiratory system, including without limitation, chronic obstructive pulmonary disease (COPD), asthma, emphysema bronchospasm, and the like.

The terms "treat" and "treatment" in connection with a method of treatment are used interchangeably and are meant to indicate the taking of steps to obtain beneficial or desired clinical results in an individual suffering from disease, including the postponement of further disease progression, or reduction in the severity of symptoms that have or are expected to develop, ameliorating existing symptoms and preventing additional symptoms.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

BRIEF DESCRIPTION OF THE FIGURES

FIG. 11 is a diagram of the testing apparatus for testing free moving guinea-pigs.

DETAILED DESCRIPTION OF THE INVENTION

Figure 1:
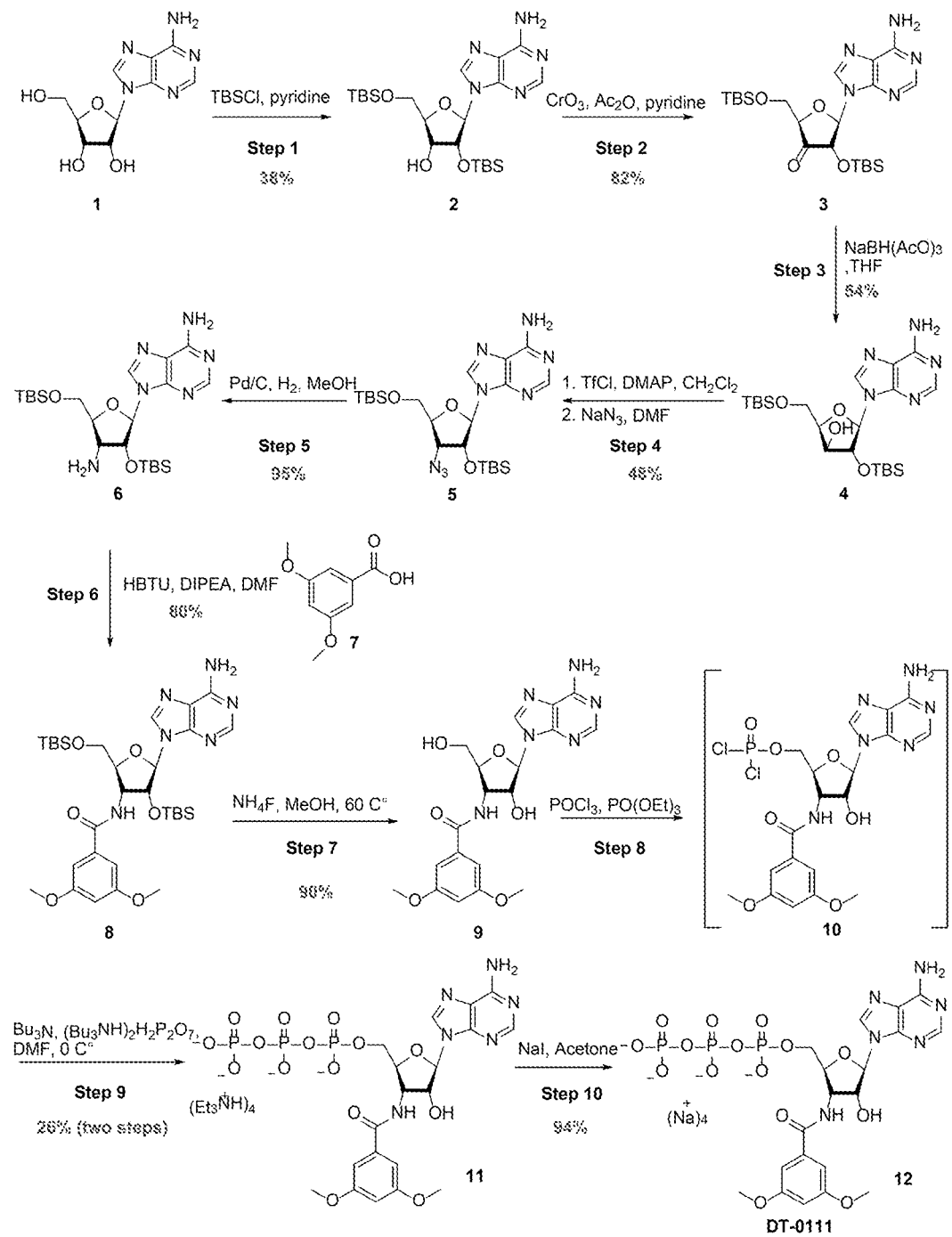
FIG. 1 is a reaction scheme for the preparation of the compound sodium 3'-N-(3",5"-dimethoxybenzoyl)-3'-deoxy-β-D-adenosine 5'-triphosphate.

Provided are compounds of Formula (I) and pharmaceutically acceptable salts, solvates, coordination complexes and prodrugs thereof, and methods of treatment and uses thereof. As demonstrated in the examples that follow, the compounds of the invention function as antagonists of P2X3R and/or P2X2/3R.

The compounds are thus suitable for treatment of disorders that are mediated or driven by activation of P2X3R and/or P2X2/3R. Such disorders include, for example, respiratory disorders; pain; and disorders of the bladder.

Synthesis of Compounds

The compounds of Formula (I) may be prepared by the following Scheme 1 which begins with commercially available or readily synthesizable starting compounds:

13 14
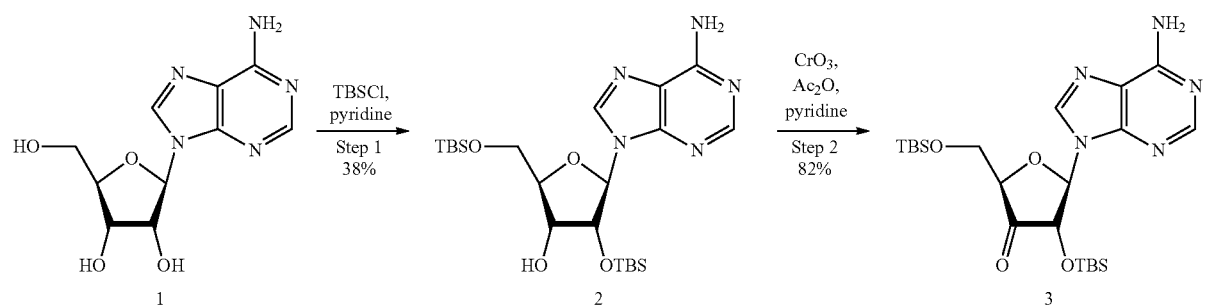
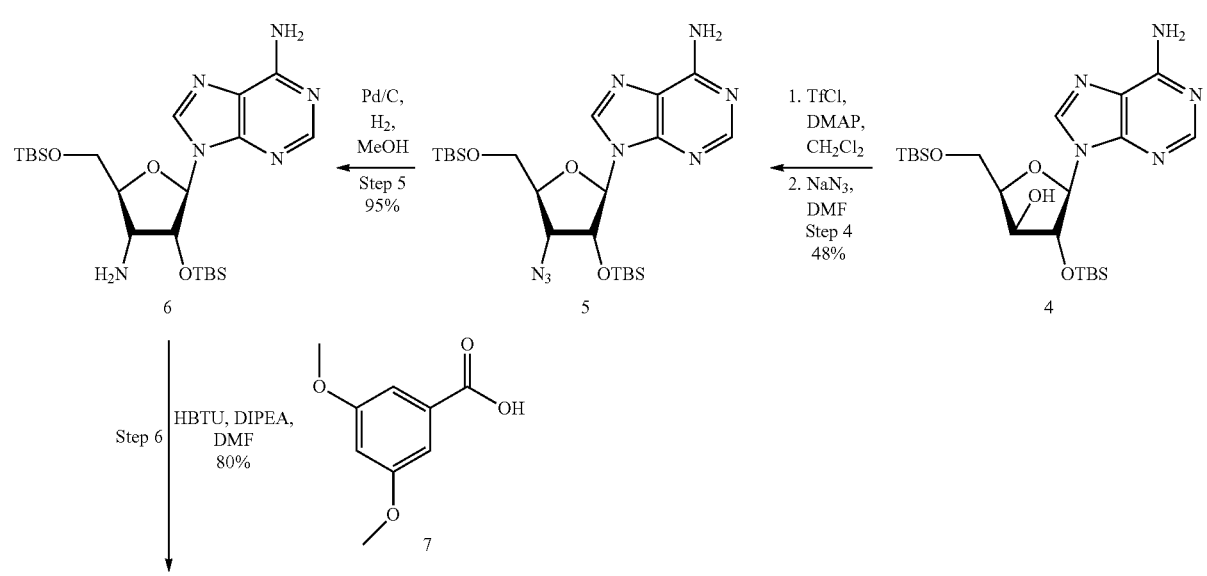
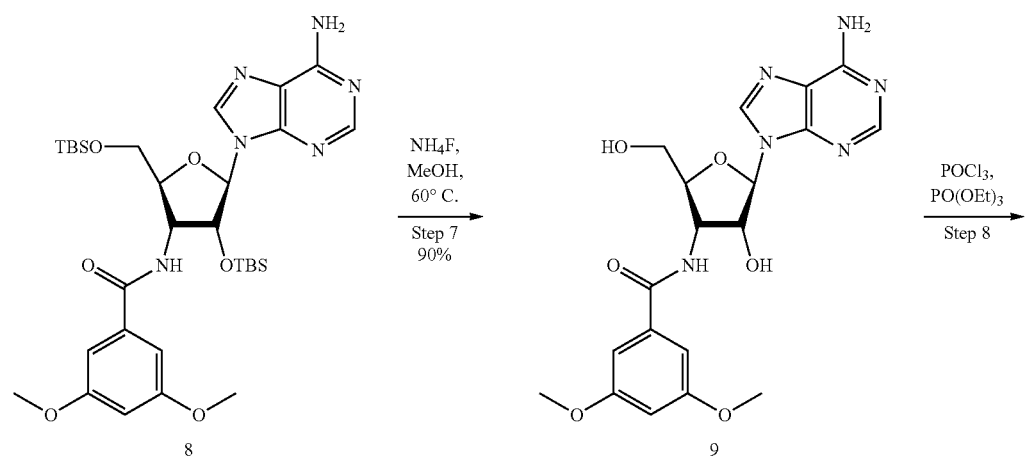

-continued

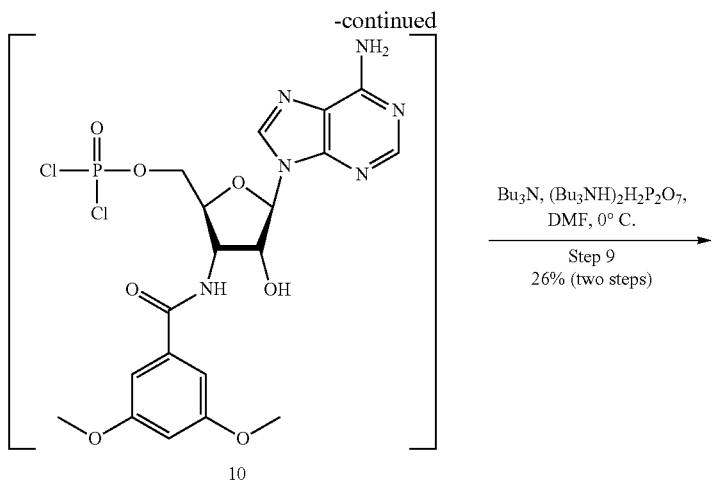

10

Bu₃N, (Bu₃NH)₂H₂P₂O₇,
DMF, 0° C.
―――――――――→
Step 9
26% (two steps)

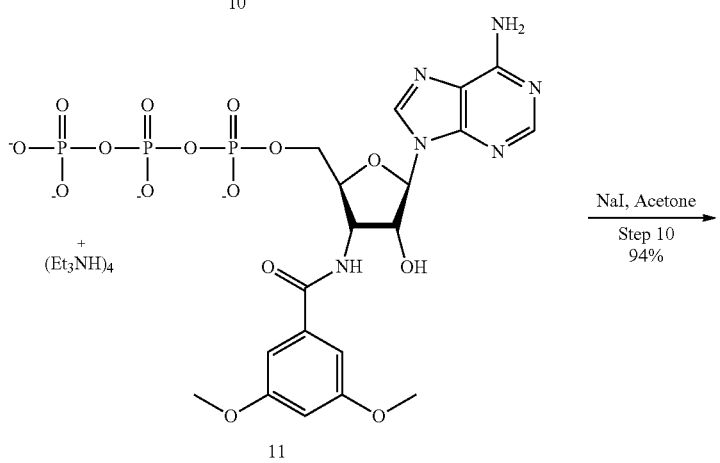

11

NaI, Acetone
―――――――→
Step 10
94%

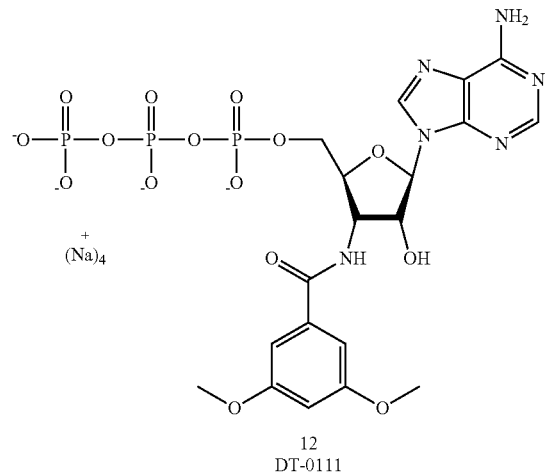

12
DT-0111

The synthesis is carried out for example in the following manner:

Synthesis of 2',5'-Bis-O-(tert-butyldimethylsilyl)-β-D-adenosine (2)

In a 2 L round bottom flask, TBDMSCl (169.2 g, 1.12 mol) was added to a suspension of adenosine (100 g, 0.37 mol) in pyridine (800 mL) and the mixture was stirred at room temperature for 48 h. TLC of the reaction (EtOAc: Hexanes=2:1) showed three spots: 2',3',5'-tris-O-(tert-butyldimethylsilyl)-β-D-adenosine (upper spot, $R_f$=0.58), 2',5'-tris-O-(tert-butyldimethylsilyl)-β-D-adenosine (middle spot, $R_f$=0.36), 3',5'-tris-O-(tert-butyldimethylsilyl)-β-D-adenosine (lower spot, $R_f$=0.19). The solvent was evaporated, and the crude was dissolved in $CH_2Cl_2$, washed with ice-cold 4% HCl. After separation of aqueous layer, the organic layer was washed with saturated $NaHCO_3$, $H_2O$, brine, and dried over anhydrous $Na_2SO_4$. After evaporation of solvent, the crude white solid was dissolved in $CH_2Cl_2$ (600 mL) and purified by silica gel column chromatography (portion wise, 330 g ISCO column, Hexanes/EtOAc—0 to 100% EtOAc). After three column chromatographic purifications, the product-enriched mixture of fractions were combined and concentrated. Recrystallization from CHCl$_3$/Et$_2$O afforded the desired product (2) as a pure white solid. Multiple recrystallizations gave 70 g of expected product (2) (38%).

Synthesis of 9-[2',5'-Bis-O-(tert-butyldimethylsilyl)-β-D-erythro-pentofuran-3-ulosyl]-9H-adenine (3)

In a 2 L round-bottom flask, pyridine (19.5 mL, 242.4 mmol) and Ac$_2$O (11.5 mL, 121.2 mmol) were added to an ice-cold suspension of CrO$_3$ (12.1 g, 0.12 mol) in CH$_2$Cl$_2$ (400 mL) and the brown slurry was stirred for 30 min until homogeneous, then warmed to room temperature. A solution of compound (2) (30 g, 60.6 mmol) in CH$_2$Cl$_2$ (300 mL) was added and stirring was continued for 2 h. TLC showed that the reaction was complete ($R_f$=0.41, EtOAc:Hexane=2:1). The reaction mixture was poured into cold EtOAc (2 L) and filtered. The filtrate was washed with saturated NaHCO$_3$, H$_2$O brine, and dried over anhydrous Na$_2$SO$_4$. After evaporation of solvent, the solid product was precipitated out and filtered, to afford 22.4 g of the expected product (3). The filtrate was concentrated and purified by silica gel chromatography (ISCO 220 g column, Hexanes/EtOAc—0 to 100% EtOAc), to afford 2.3 g product. The combined yield of the white solid product (3) was 24.7 g (82%).

Synthesis of 9-[2',5'-Bis-O-(tert-butyldimethylsilyl)-β-D-xylofuranosyl]-9H-adenine (4)

In a 1 L round-bottom flask, to an ice-cold solution of ketone (3)(24.7 g, 50.1 mmol) in THF (400 mL) was added NaBH(OAc)$_3$ (21.2 g, 100.1 mmol) and the mixture was stirred for 72 h at room temperature. TLC showed incomplete reaction and there was still some starting material left ($R_f$=0.36, EtOAc:Hexane=2:1). After evaporation of the solvent, the crude was dissolved in EtOAc and washed with saturated NaHCO$_3$, H$_2$O, brine, and dried over anhydrous Na$_2$SO$_4$. After evaporation of solvent, the crude was purified by silica gel chromatography (ISCO 220 g column, Hexane/EtOAc—0 to 100% EtOAc). Multiple column purifications were needed in order to remove the stereoisomer (2) which was generated during the reduction. 13.5 g white solid product (4) was obtained (54%).

Synthesis of 3'-Azido-3'-deoxy-2',5'-Bis-O-(tert-butyldimethylsilyl)-β-D-adenosine (5)

In a 1 L round-bottom flask, TfCl (3.2 mL, 30.1 mmol) was added to an ice-cold solution of (4) (13.5 g, 27.3 mmol) and DMAP (10 g, 81.8 mmol) in CH$_2$Cl$_2$ (250 mL). The mixture was stirred for 15 min. TLC showed incomplete reaction and there was still some starting material left ($R_f$=0.5, EtOAc:Hexane=2:1). A second portion of TfCl (0.7 mL, 6.5 mmol) was added and continued to stir for 30 min. The reaction was partitioned (ice-cold 1% aqueous AcOH/CH$_2$Cl$_2$) and the aqueous layer was extracted with CH$_2$Cl$_2$. The combined organic phase was washed with ice-cold saturated NaHCO$_3$, ice-cold brine and dried over anhydrous Na$_2$SO$_4$. After evaporation of solvent, the off-white foam product was used in the next step directly.

NaN$_3$ (8.8 g, 136.4 mmol) was added into a solution of above triflate intermediate in DMF (300 mL) and the reaction was stirred at room temperature overnight. TLC showed the expected product ($R_f$=0.47, EtOAc:Hexane=2:1). The reaction was concentrated and the crude was dissolved in EtOAc and washed with saturated NaHCO$_3$, H$_2$O, brine, and dried over anhydrous Na$_2$SO$_4$. After evaporation of solvent, the crude was purified by silica gel chromatography (ISCO 330 g column, Hexane/EtOAc—0 to 100% EtOAc). 6.9 g white foam product (5) was obtained (48%).

Synthesis of 3'-Amino-3'-deoxy-2',5'-Bis-O-(tert-butyldimethylsilyl)-β-D-adenosine (6)

A solution of compound (5) (6.9 g, 13.2 mmol) in MeOH (300 mL) was hydrogenated at ambient pressure (H$_2$ balloon) in the presence of 10% Pd/C (1.0 g) overnight. The mixture was filtered through a pad of celite. After evaporation of solvent, off-white solid product (6) was obtained (6.4 g, 97%).

Synthesis of 3'-N-(3",5"-dimethoxybenzoyl)-3'-deoxy-2',5'-Bis-O-(tert-butyldimethylsilyl)-β-D-adenosine (8)

To a solution of 3,5-dimethoxybenzoic acid (7) (2.4 g, 12.9 mmol) in anhydrous DMF (100 mL) was added HBTU (4.9 g, 12.9 mmol) and the mixture was stirred for 30 min at room temperature. While the reaction was cooled in an ice-water bath, a solution of compound (6) (6.4 g, 12.9 mmol) in DMF (50 mL, anhydrous) was added, followed by the addition of DIPEA (4.5 mL, 25.9 mmol). The reaction was stirred overnight, allowed to warm to room temperature. TLC showed the completion of reaction ($R_f$=0.5, EtOAc:Hexane=2:1). The reaction was concentrated, and the crude was dissolved in EtOAc and washed with saturated NaHCO$_3$, H$_2$O, brine, and dried over anhydrous Na$_2$SO$_4$. After evaporation of solvent, the crude was purified by silica gel chromatography (ISCO 120 g column, Hexane/EtOAc—0 to 100% EtOAc). The product-enriched mixture fractions were combined and concentrated. Recrystallization from EtOAc/Hexane was performed and pure white solid (8) was obtained (6.8 g, 80%).

Synthesis of 3'-N-(3",5"-dimethoxybenzoyl)-3'-deoxy-β-D-adenosine (9)

A solution of (8)(7.8 g, 11.8 mmol) and NH$_4$F (3.9 g, 106.5 mmol) in MeOH (600 mL) was stirred in 60° C. oil bath for 12 h. The clear reaction solution became cloudy after heating for 1 h and changed to white slurry. The reaction was cooled to room temperature and the solid was filtered. Pure white solid product (9) was obtained (4.6 g, 90%).

Synthesis of tetra-triethylammonium 3'-N-(3,5-dimethoxybenzoyl-3'-deoxy-β-D-adenosine 5'-triphosphate (11)

POCl$_3$ (0.4 mL, 4.6 mmol) was added to an ice-cold solution of compound (9)(1 g, 2.3 mmol) in triethylphosphate (30 mL) and the reaction mixture was stirred for 3 h at 0-4° C., giving the dichlorophosphoridate intermediate (10).

Under 0° C., tri-n-butylamine (1.1 mL, 4.6 mmol) was added to the solution, followed by the addition of bis(tri-n-butylammonium) pyrophosphate (5.1 g, 9.3 mmol) solution in DMF (25 mL). The reaction was stirred at 0-4° C. for 2 h. A solution of 0.2 M triethylammonium bicarbonate buffer (pH=7.3) was added into the reaction mixture and stirred at 0-4° C. for 1 h. The solution was allowed to reach room temperature upon stirring and then left standing in the freezer overnight.

Triethylphosphate was extracted with tert-butyl methyl ether and the aqueous solution was evaporated and applied to C18 reverse phase column chromatography (80 g, C18, ISCO, $CH_3CN/0.025$ M TEAB buffer, pH=7.3). The fractions containing the expected product were collected and concentrated, then lyophilized.

The crude 5'-triphosphate adenosine was purified by ion exchange chromatography on Sephadex A- $^-HCO_3$ form with TEAB buffer, pH=7.3. After equilibration of the column with water, the crude product was dissolved in $H_2O$ (5 mL) and loaded onto the column. The column was washed with $H_2O$ (300 mL), followed by 0.1 M-0.5 M TEAB (pH=7.3) buffer elution (200 mL/each concentration). The expected product was eluted out at 0.5 M TEAB buffer and the combined fractions were concentrated, lyophilized. 960 mg white foam product (11) was obtained [26%, based on integration $^1H$ NMR, them was 30% of excess $(Et_3NH^+)(^-OAc)$].

Synthesis of Sodium 3'-N-(3,5-dimethoxybenzoyl)-3'-deoxy-β-D-adenosine 5'-triphosphate (12, DT-0111)

To a solution of tetra-triethylammonium phosphate (11) (1.1 g, 0.93 mmol) in MeOH (3.5 mL) was added 1M NaI solution in acetone (9.5 mL, 9.3 mmol). While stirring, a white solid precipitated out. Additional 10 mL acetone was added, and the white slurry was stirred for 10 min. The mixture was transferred into centrifuge tube and centrifuged (2 min, 3000 rpm). The solvent was decanted. Another 10 mL acetone was added to wash the solid and centrifuged, decanted (repeated two more times). The white solid was dried under vacuum, giving 730 mg of DT-0111 (94%).

Salts, Solvates, Coordination Complexes and Prodrugs

The compounds of the present invention may take the form of salts. The term "salts" embraces addition salts of free acids or free bases which are compounds of the invention. The term "pharmaceutically acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention. Both mono and polyanionic salts are contemplated, depending on the number of acidic hydrogens available for deprotonation.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, pivalic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Pharmaceutically acceptable salts of compounds of the present invention can also be formed using organic and inorganic bases. Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic organic amines such as, for example, N,N'-dibenzylethylenediamine, chloroprocaine, choline, diethanolamine, ethylenediamine, tromethamine, meglumine (N-methylglucamine), procaine, morpholine, thiomorpholine, piperidine, pyrrolidine, a mono-, di- or tri-lower alkylamine (e.g., ethyl-, tert-butyl-, diethyl-, diisopropyl-, triethyl-, tributyl- or dimethylpropylamine), or a mono-, di-, or trihydroxy lower alkylamine (e.g., mono-, di- or triethanolamine). In one embodiment, the salt is a triethylammonium salt of a compound of Formula (I).

All of these salts may be prepared by conventional means from the corresponding compound according to Formula (I) by reacting, for example, the appropriate acid or base with the compound according to Formula (I). Preferably the salts are in crystalline form, and preferably prepared by crystallization of the salt from a suitable solvent. The person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

An exemplary salt of the compound of Formula (I) is depicted below:

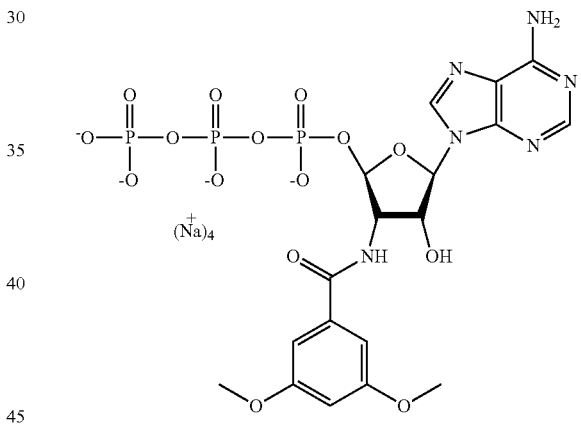

Compounds of Formula (I) may exist in unsolvated as well as solvated forms with pharmaceutically acceptable solvents such as water, ethanol, and the like, and it is intended that the invention embrace both solvated and unsolvated forms. "Solvate" means a physical association of a compound with one or more solvent molecules. "Solvate" includes solvent addition forms that contain either stoichiometric or non-stoichiometric amounts of solvent. This physical association involves varying degrees of ionic and covalent bonding, including hydrogen bonding. In certain instances, the solvate will be capable of isolation, for example when one or more solvent molecules are incorporated in a crystal lattice of a crystalline solid. "Solvate" encompasses both solution-phase and isolatable solvates. If the solvent is water, the solvate formed is a "hydrate"; when the solvent is alcohol, the solvate formed is an alcoholate. Non-limiting examples of solvates thus include hydrates, ethanolates, methanolates, and the like. Preparation of solvates is generally known. For example, M. Caira et al, *J. Pharmaceutical Sci.*, 93(3), 601-611 (2004) describe the preparation of the solvates in ethyl acetate as well as from water. Similar preparations of solvates, hydrates and the like are described by van Tonder et al, *AAPS PharmSciTech,* 5:86 (2004); and Bingham et al, *Chem. Commun.,* 7:603-604 (2001). A typical, non-limiting, process for solvate formation involves dissolving compound in desired amounts of the desired solvent (organic or water or mixtures thereof) at a higher than room temperature, and cooling the solution at a rate sufficient to form crystals which are then isolated by standard methods.

Also included in the present invention are compounds of Formula (I) that are pharmaceutically acceptable coordination complexes with metal ions. For example, a metal can coordinate to one or more of the Lewis bases present in the ATP reagent (e.g., an oxygen present in the phosphate side chain of the ATP reagent). The metal can be any metal, including but not limited to alkali metals, alkaline earth metals (e.g., Mg.$^{2+}$ or $Ca^{2+}$), lanthanides, actinides, and transition metals (e.g., $Cr^{3+}$ or $Co^{3+}$). In certain embodiments the active agent is complexed with $Mg^{2+}$ ions.

Pharmaceutically acceptable prodrugs of compounds of Formula (I) are also contemplated. A discussion of prodrugs is provided in T. Higuchi and V. Stella, *Pro-drugs as Novel Delivery Systems* (1987) 14, ACS. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a compound of Formula (I), or a pharmaceutically acceptable salt, solvate or coordination compound thereof. The transformation may occur by various mechanisms (e.g., by metabolic or chemical processes), such as, for example, through hydrolysis in blood. For a discussion on the principles of prodrug design, see Bundegaard, H. *Design of Prodrugs*, Elsevier, New York-Oxford (1985).

Pharmaceutical Compositions

The compounds of the invention may be administered in the form of a pharmaceutical composition. A pharmaceutical composition may be prepared comprising a pharmaceutically acceptable carrier and a compound of Formula (I), or pharmaceutically acceptable salt, solvate, coordination complex or prodrug thereof. The active ingredient or agent in such formulations may comprise from 0.1 to 99.99 weight percent of the formulation. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., Remington's Pharmaceutical Sciences, 18th Edition (1990), Mack Publishing Co., Easton, Pa. Suitable dosage forms may comprise, for example, aerosol, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl or propyl paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents, absorbents or lubricating agents. According to one tablet embodiment, the active agent may be combined with carboxymethylellulose calcium, magnesium stearate, mannitol and starch, and then formed into tablets by conventional tableting methods.

For inhalation administration the active agent is delivered as fine particles by a dry-powder medical device, i.e., an inhaler, or alternatively, dissolved in physiologic saline solution, which is delivered by a metered-dose inhaler or nebulizer that deliver a specific amount of aerosolized medication.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres also known as nano-particles.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

In one embodiment, the active compound may be rendered in the form of an aqueous solution, such as the aqueous solutions described in US Pat. Pub. 2010/0222294 for delivery of ATP and ATP analogs. The solution may be administered by the intranasal or intratracheal route (inhalation), for example. Such solutions can contain the active agent and auxiliary agents such as glycine, buffered to a pH of about 8.7 to 9.5. Solutions with other pH values are possible. The solutions can further contain a biocompatible buffer, e.g., a phosphate buffer such as a phosphate buffer that contains $Na_2HPO_4$ and/or $K_2HPO_4$. The biocompatible buffer can also be a bicarbonate buffer, an acetate buffer, a citrate buffer, or a glutamate buffer. In addition, any of the solutions can contain one or more of 1,3-bis[tris(hydroxymethyl)methylamino]propane (Bis-Tris Propane); tris(hydroxy) aminomethane (Tris); tris(hydroxymethyl)aminomethane (Trizma); 4-(2-hydroxyethyl)-1-piperazinepropanesulfonic acid (EPPS); N-[tris(hydroxymethyl) methyl]glycine (Tricine); glycine; diglycine (Gly-Gly); N,N-Bis(2-hydroxyethyl)glycine (bicine); N-(2-hydroxyethyl)piperazine-N'-(4-butanesulfonic acid) (HEPBS); N-[tris(hydroxymethyl)methyl]-3-aminopropanesulfonic acid (TAPS); 2-Amino-2-methyl-1,3-propanediol (AMPD); N-tris(Hydroxymethyl)methyl-4-aminobutanesulfonic acid (TABS); N-(1,1-dimethyl-2-hydroxyethyl)-3-amino-2-hydroxypropanesulfonic acid (AMPSO); 2-(cyclohexylamino) ethanesulfonic acid (CHES); 3-(cyclohexylamino)-2-hydroxy-1-propanesulfonic acid (CAPSO); or β-aminoisobutyl alcohol (AMP).

The solution can further contain a stabilizer. The stabilizer can be a chelating agent, e.g., ethylenediaminetetraacetic acid (EDTA) or ethylene glycol tetraacetic acid (EGTA). The stabilizer can also be a sugar alcohol (e.g., sorbitol, mannitol, adonitol, erythritol, xylitol, lactitol, isomalt, maltitol, or a cyclitol), glycerol, methionine, or creatinine.

For administration by inhalation, the appropriate solutions or compositions are delivered in the form of an aerosol spray from pressured container or dispenser which contains a suitable propellant, e.g., a gas such as carbon dioxide, or a nebulizer.

Administration Methods

The compounds of Formula I, including pharmaceutically acceptable salts thereof, may be administered by any route, including oral, rectal, sublingual, aerosol and powder inhalation, and parenteral administration. Parenteral administration includes, for example, intravenous, intramuscular, intraarterial, intraperitoneal, intranasal, intratracheal (e.g., by inhaler), intravesical (e.g., to the bladder), intradermal, transdermal, topical or subcutaneous administration. Also contemplated within the scope of the invention is the instillation of a drug in the body of the patient in a controlled formulation, with systemic or local release of the drug to occur at a later time. For example, the drug may be localized in a depot for controlled release to the circulation, or for release to a local site.

The specific dose of a compound according to the invention to obtain therapeutic benefit will, of course, be determined by the particular circumstances of the individual patient including the size, weight, age and sex of the patient, the nature and aggressiveness of the disorder treated, and the route of administration of the compound. Dosage regimens may be adjusted by the physician to provide the optimum therapeutic response. For example, the physician may wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents. The dosage may be administered once daily, although dividing this recommended daily dose to provide multiple administrations is possible.

For example, a daily dosage from about 0.05 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. The compositions are preferably formulated in a unit dosage form, each dosage containing from about 1 to about 500 mg, more typically, about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The treatment may be carried out for as long a period as necessary, either in a single, uninterrupted session, or in discrete sessions. The treating physician will know how to increase, decrease, or interrupt treatment based on patient response. The treatment schedule may be repeated as required.

One or more compounds useful in the practice of the present invention may be administered simultaneously, by the same or different routes, or at different times during treatment. The compounds may be administered before, along with, or after other medications.

Treatment of Respiratory Disease

According to another embodiment of the invention, a method for treating a respiratory disease in a subject in need of such treatment is provided, wherein the respiratory symptoms are mediated by P2X3R and/or P2X2/3R activation. Thus, the compounds of the invention are believed useful for treating respiratory disorders that may be mediated by administration of a P2X3R and/or P2X2/3R antagonist. The method of treatment comprises administering to a subject in need of such treatment a therapeutically effective amount of a compound according to Formula (I), or a pharmaceutically acceptable salt, solvate, coordination complex or prodrug thereof.

Figure 4:
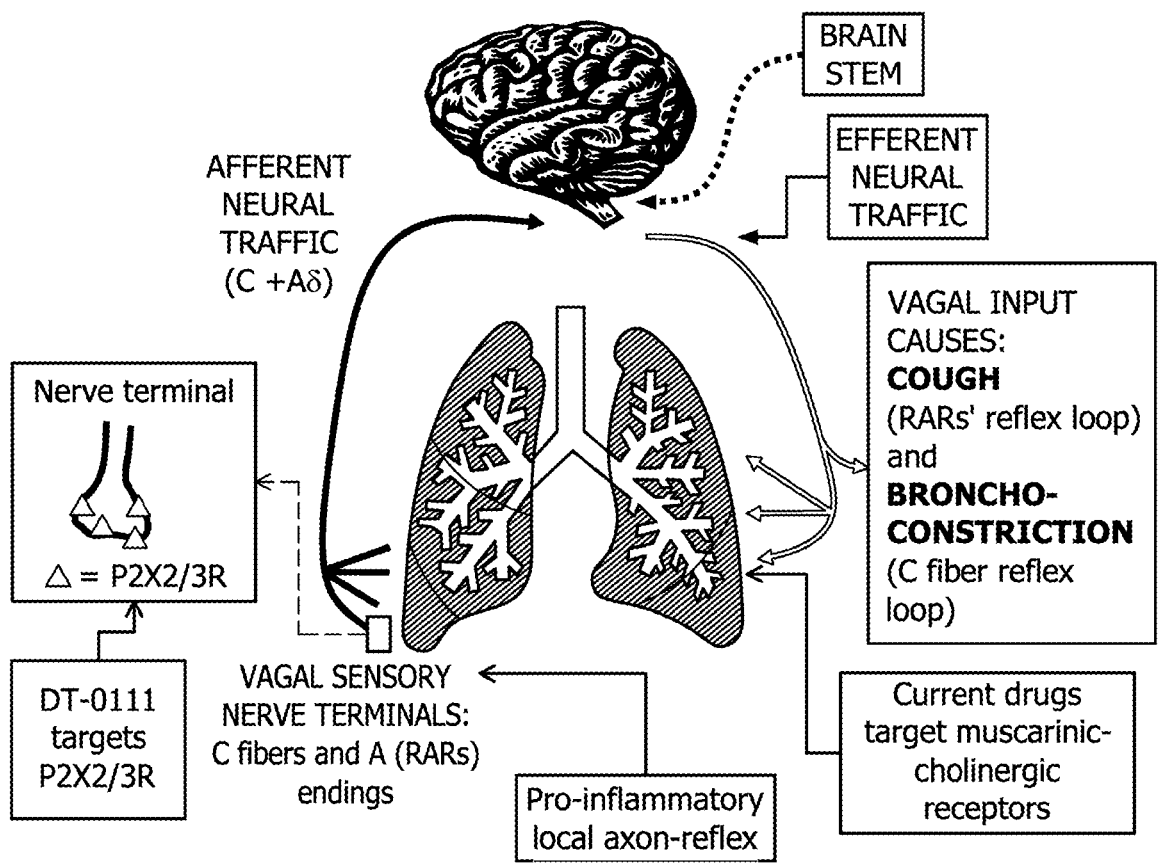
FIG. 4 shows a schematic representation of the activation of P2X3R and/or P2X2/3R stimulates vagal sensory nerve terminals in the lungs to cause bronchoconstriction, the induction of cough and the localized release via an axon reflex of neuro-peptides that are proinflammatory.

In some embodiments, the respiratory disease is chronic obstructive pulmonary disorder (COPD), bronchospasm, emphysema, cough or asthma. As shown in FIG. 4 the activation of P2X3R and/or P2X2/3R stimulates vagal sensory nerve terminals in the lungs to cause bronchoconstriction, the induction of cough and the localized release via an axon reflex of neuro-peptides that are proinflammatory.

P2X2/3R are mechanistically involved in activation of vagal C-fibers and rapidly adapting receptors (Aδ-fibers) that are believed to be central to cough initiation and sensitization (Undem et al., Respir Physiol Neurobiol 167 (1):36-44, 2009). Using the selective P2X3R, P2X2/3R antagonist A-317491 (Abbott), it has been shown that ATP activation of airways afferents is mediated by P2X3R (Kwong et al., Am J Physiol Lung Cell Mol Physiol 292:L85 g-L865, 2008). Thus, in some embodiments, the compounds of the present invention, which are P2X3R and P2X2/ antagonists, are administered for the treatment of a respiratory disease which is a cough related respiratory disease or disorder. "Cough related respiratory disease" refers to, without limitation, cough hypersensitivity syndrome, chronic obstructive pulmonary disease (COPD), asthma, bronchospasm, and the like. "Cough related respiratory disorders" include, for example, sub-acute cough (a cough lasting between two and eight weeks) or chronic cough (persistent or refractory cough lasting longer than eight weeks that may not have an obvious underlying cause and is may not be associated with other respiratory diseases), treatment-resistant cough, idiopathic chronic cough, cough associated with upper respiratory infection, post-viral cough, iatrogenic cough (e.g., as induced by ACE-inhibitors), idiopathic pulmonary fibrosis or cough associated with smoking or a form of bronchitis.

Cough related respiratory disorders can include the urge to cough associated with any respiratory disease, for example urge to cough associated with chronic obstructive pulmonary disease (COPD), cough-variant asthma, interstitial lung disease, or whooping cough. For example, the invention relates to a method of treatment of the symptoms of cough and/or urge to cough associated with a respiratory disease or disorder mediated by a P2X3R and/or P2X2/3R antagonist. Antagonism of P2X3R with the P2X3R antagonist AF-219 has been shown to be effective in a trial of refractory chronic cough, indicating the role the P2X3 receptor in mediation of cough neuronal hypersensitivity underlying cough, and the utility of P2X3 receptor antagonists in the treatment of neuronal hypersensitivity underlying acute, sub-acute or chronic cough (Abdulqawi et al., Lancet. 2015; 385(9974):1198-1205); U.S. Pat. No. 9,284,279.

In particular embodiments of the invention, the respiratory disease treated includes chronic cough. In one such embodiment, the aim of the treatment is to reduce daytime cough in idiopathic/treatment-resistant chronic cough. In other embodiments, the chronic cough treated is not caused by an underlying disease or ailment. For instance, the chronic cough can be caused by persistent endogenous over-activation of a P2X3R and/or a P2X2/3. Such activation may not be the result of a separate ailment.

Treatment of Disorders of the Bladder

P2X3R and P2X2/3R are located on both peripheral and central terminals of primary afferents and implicated in various sensory functions in the urinary bladder (Khakh and north, Nature 442:527-532, 2006). Urinary bladder sensation requires the activation by ATP of P2X3/P2X2/3 receptors located in bladder afferent C-fibers.

P2X3R and/or P2X2/3R antagonists have been described as useful for the treatment of various forms of disorders of the bladder, including bladder overactivity, urinary incontinence and interstitial cystitis. See, e.g., US Pat. Pub. 2004/0019042. The P2X3/P2X2/3 receptors on bladder afferent nerves have been shown to positively regulate sensory activity and non-voiding contractions in overactive bladders, and are modulated by the P2X3/P2X2/3 antagonist AF-353 (Munroz et al., BJUI International, 110(8b):E409-E414, 2012). The P2X3-P2X2/3 antagonist A-317491 has been shown to inhibit cyclophosphamide (CYP)-induced cystitis in experimental animals, thus demonstrating utility for treatment bladder overactivity (Ito et al., Naunyn-Shmied Arch Pharmacol (2008) 377: 483. Further evidence of the involvement of P2X3/P2X2/3 receptors in control of bladder activity, and the successful modulation of those sensors by a P2X3/P2X2/3 antagonist, has been shown with the selective P2X3-P2X2/3 antagonist AF-792 (5-(5-ethynyl-2-isopropyl-4-methoxy-phenoxy)-pyrimidine-2,4-diamine, previously known as RO-5) (Yaan et al., Journal of Neuoscience, 30(12):4503-4507, 2010). Accordingly, provided is a method of treatment of disorders of the bladder comprising administering to a subject in need of such treatment a therapeutically effective amount of a compound according to Formula (I), or a pharmaceutically acceptable salt, solvate, coordination complex or prodrug thereof, the aforesaid compounds being P2X3R and P2X2/3R antagonists. Disorder of the bladder believed treatable include, but are not limited to bladder overactivity, urinary incontinence and interstitial cystitis. Included within treatment of balder overactivity is the treatment of the various pathologies characterized as overactive bladder, which includes, for example, urinary urgency, urinary frequency, altered bladder capacity, micturition threshold, unstable bladder contractions, sphincteric spasticity, detrusor hyperreflexia (neurogenic bladder), detrusor instability, and the like. Interstitial cystitis is a chronic symptom-complex characterized by pathological sensation of the bladder without evidence of bacterial cystitis or other identifiable lower urinary tract disease. Patients with Interstitial cystitis typically describe feeling the urge to void frequently, as well as pain in the bladder and/or urethra.

Treatment of Pain

P2X3R subunits are expressed predominately and selectively in C- and Aδ-fiber primary afferent neurons in most tissues and organ systems, including skin, joints, and hollow organs, indicating a high degree of specificity to the pain sensing system in the human body. Thus, compounds such as the compound of the present invention, which block or inhibit the activation of P2X3-containing receptors, serve to block the activation of these fibers by ATP and thus block pain stimulus. Accordingly, provided is a method of treatment of pain, comprising administering to a subject in need of such treatment a therapeutically effective amount of a compound according to Formula (I), or a pharmaceutically acceptable salt, solvate, coordination complex or prodrug thereof.

For a review of antagonism of P2X3R and P2X2/3R for the treatment of chronic pain and afferent sensitization, see Ford, Purinergic Signal. 8 (Suppl. 1) 3-26 (2012).

As antagonists of P2X3R, the compounds of the invention find utility in the treatment of pain, encompassing both nociceptive and neuropathic pain, including both acute, sub-acute and chronic pain. The compounds are expected to find utility as analgesics in the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

The practice of the invention is illustrated by the following non-limiting examples. The skilled person skilled in the art will appreciate that it may be necessary to vary the procedures for any given embodiment of the invention. For example, reaction monitoring, such as by using thin layer chromatography, or HPLC may be used to determine the optimum reaction time. Products may be purified by conventional techniques that will vary, for example, according to the amount of side products produced and the physical properties of the compounds. On a laboratory scale, recrystallization from a suitable solvent, column chromatography, normal or reverse phase HPLC, or distillation are all techniques which may be useful. The person skilled in the art will appreciate how to vary the reaction conditions to synthesize any given compound within the scope of the invention without undue experimentation. See, e.g., Vogel's Textbook of Practical Organic Chemistry, by A. I. Vogel, et al., Experimental Organic Chemistry: Standard and Microscale, by L. M. Harwood et al. (2nd Ed., Blackwell Scientific Publications, 1998), and Advanced Practical Organic Chemistry, by J. Leonard, et al. (2nd Edition, CRC Press 1994).

EXAMPLES

3",5"-Dimethoxybenzoyl-3'-amino-3'-deoxyadenosine-5'-triphosphate Triethyl Ammonium Salt (Compound 11)

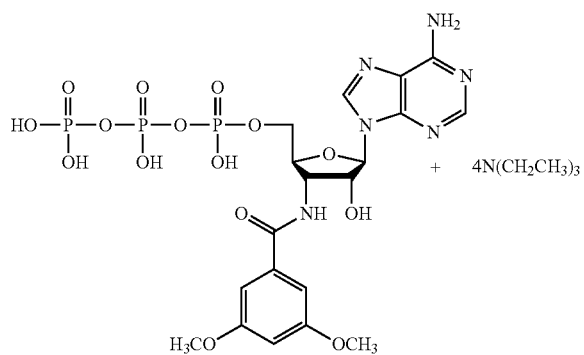

Compound 11 was prepared according to the scheme of FIG. 1, and described in further detail above. Compound numbering in this example corresponds to the compound numbering in FIG. 1.

Example 1: Selectivity

Functional assays in vitro carried out by the Department of Pharmacology of the University of North Carolina (PDSP) have shown that DT-0111 does not act as an agonist or antagonist at the following receptors: P2Y2, P2Y4, P2Y6, P2Y1, P2Y12, P2Y13 and P2Y14. The assays were carried out utilizing the method set forth in Kroeze et al., PRESTO-Tango as an open-source resource for interrogation of the druggable human GPCRome, Nat. Struct. Mol. Biol. 2015 May; 22(5):362-9.

Example 2: Nodose Ganglion Neuron Assay of P2X2/3 Receptor Antagonism by 3",5"-Dimethoxybenzyl-3'-Amino-3'-Deoxyadenosine-5'-Triphosphate Triethyl Ammonium Salt The following assay demonstrates the P2X2/3 receptor antagonism effect of compounds of Formula (I).

ATP and the agonist α,β-methylene-adenosine 5'-triphosphate (α,β-meATP) were obtained from Sigma Chemical Company (Poole, UK).

Single neurons were enzymatically isolated from rats' nodose ganglia as described by Zhong et al., Br J Pharmacol 1998; 125, 771-781. Briefly, 17- day old male Sprague-Dawley rats were killed by $CO_2$ inhalation. Ganglia were rapidly dissected and placed in Leibovitz's L-15 medium (Life Technologies, Paisley, UK). Ganglia were desheathed, cut and incubated in 4 ml $Ca^{2+}/Mg^{2+}$-free Hanks' balanced salt solution with 10 mm Hepes buffer (pH 7.0) (HBSS) (Life Technologies) containing 1.5 mg ml-1 collagenase (Class-II; Worthington Biochemical Corporation, Reading, UK) and 6 mg ml-1 bovine serum albumin (Sigma) at 37° C. for 40 min. Ganglia were then incubated with 4 ml HBSS containing 1 mg ml-1 trypsin (Sigma) at 37° C. for 20 min. The solution was replaced with 3 ml of growth medium comprising L-15 medium supplemented with 10% bovine serum, 50 ng ml-1 nerve growth factor, 0.2% $NaHCO_3$, 5.5 mg ml-1 glucose, 200 IU ml-1 penicillin and 200 μg ml-1 streptomycin. The ganglia were dissociated into single neurons by gentle trituration. The cells were then centrifuged at 160 g for 5 min, resuspended in 1 ml of growth medium, and plated onto 35 mm Petri dishes coated with 10 μg ml-1 laminin (Sigma). Cells were maintained at 37° C. in a humidified atmosphere containing 5% $CO_2$ and used between 2 and 48 hours after plating.

Whole-cell voltage-clamp recordings were performed at room temperature using an Axopatch 200B amplifier (Axon Instruments, Union City, Calif., USA). Membrane potential was held at ~60 mV. The external solution contained (mM): 154 NaCl, 4.7 KCl, 1.2 $MgCl_2$, 2.5 $CaCl_2$), 10 Hepes, 5.6 glucose, and the pH was adjusted to 7.4 using NaOH. Recording electrodes (resistance 2-4 mOhm) were filled with an internal solution which contained (mm): 56 citric acid, 3 $MgCl_2$, 10 CsCl, 10 NaCl, 40 14HEPES, 0.1 EGTA, 10 tetraethylammonium chloride, and the pH was adjusted to 7.2 using CsOH (total Cs+concentration 170 mm). Series resistance compensation of 72-75% was used in all recordings. The threshold for the minimum detectable response was set as 10 pA. Data were acquired using pCLAMP software (Axon Instruments). Signals were filtered at 2 kHz (-3 dB frequency, Bessel filter, 80 dB decade-1). Compounds (ATP; α,β-meATP; and compound 11) were applied by gravity flow from independent reservoirs through a 7-barrel manifold comprising fused glass capillaries inserted into a common outlet tube (tip diameter of ~200 μm) which was placed about 200 μm from the cell (Dunn et al., Br J Pharmacol. 1996; 117:35-42). One barrel was used to apply drug-free solution to enable rapid termination of drug application. Solution exchange measured by changes in open tip current was complete in 200 ms; however, complete exchange of solution around an intact cell was slower (<1 s). The intervals between agonist applications were 2 min. The agonist α,β-mATP was applied for 2 sec at 3 min intervals. The antagonist candidate, compound 11, was allowed to equilibrate for 2 min prior to application of agonist. All drugs were prepared from stock solutions and diluted in extracellular bathing solution to the final concentration. Traces were acquired using Fetchex (pCLAMP software) and plotted using Origin (Microcal, Northampton, Mass., USA).

Figure 2:
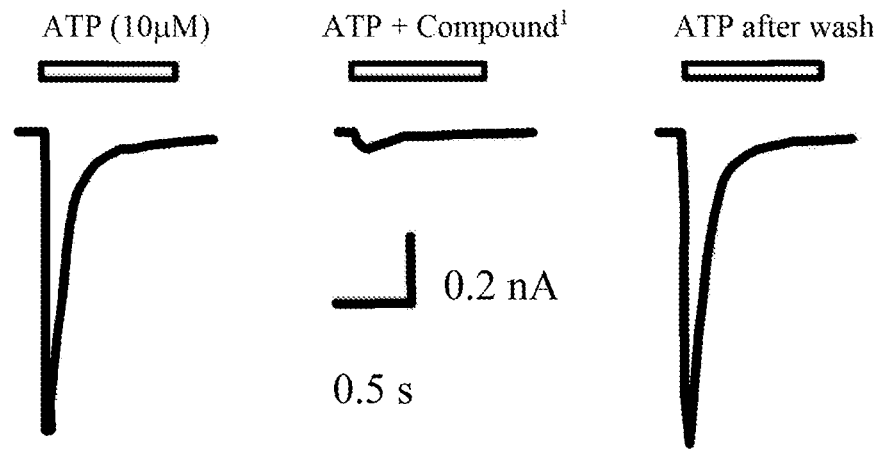
FIG. 2 contains traces generated from a native PX2/3R assay carried out using a rat nodose ganglionic cell in vitro. The compound 3",5"-dimethoxybenzoyl-3'-amino-3'-deoxyadenosine-5'-triphosphate triethylammonium salt (middle trace) substantially abrogated the receptor agonism of ATP manifested as the induction of inward current (left-hand trace). The effect is reversible, as the antagonism was abolished upon washing of the assay system, thus removing antagonist compound (right-hand trace).

The assay results are shown in FIG. 2. The bars at the top of the three traces in FIG. 2 indicate time, which is the horizontal axis of the traces. The vertical axis of the traces corresponds to current generated. Time and current scale are provided by the legend in FIG. 2. Either ATP (10 μM) or the P2X2/3 receptor agonist α,β-meATP (similar results, not shown) invoked a current as indicated in the left-hand trace of FIG. 2, demonstrating agonism of the P2X2/3 receptor. The effect was substantially abrogated by compound 11 (FIG. 2, middle trace). When the latter was washed out of the assay system, the agonist effect returned to basal levels (FIG. 2, right-hand trace). These results indicate the reversible P2X2/3 receptor antagonizing activity of compound 11.

Figure 3:
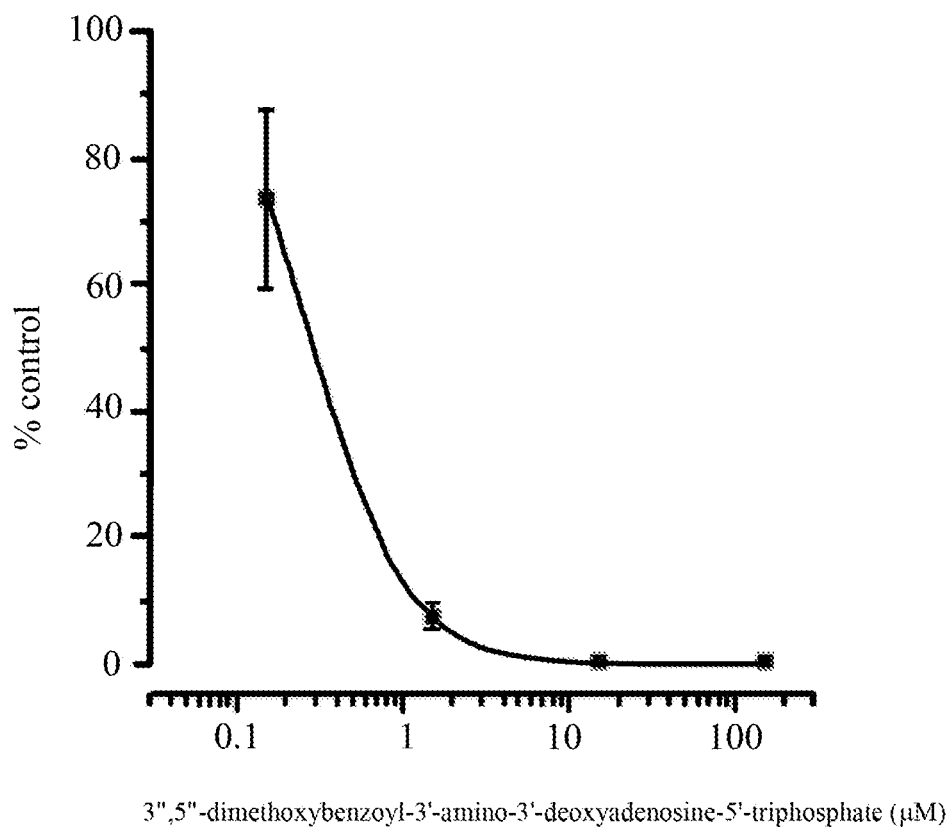
FIG. 3 is a plot of data (n=3) taken according to the assay of FIG. 1, over the four 3",5"-dimethoxybenzoyl-3'-amino-3'-deoxyadenosine-5'-triphosphate triethylammonium salt concentrations indicated in FIG. 2. The calculated $I_{c50}$ for this action was 0.3 μM.

A full concentration/effect plot was then obtained by repeating the above assay with four concentrations of compound 11 indicated in FIG. 3. At least three neurons were tested at each concentration. The results are shown in FIG. 3, demonstrating that P2X2/3 receptor antagonizing activity of compound 11 is dose-dependent, achieving complete antagonism at the higher concentrations. The curve in FIG. 3 corresponds to an $IC_{50}$ of 300 μM for compound 11 in the conditions of the assay.

Example 3 Effect of DT-0111 on ATP-Induced Neural Action Potentials in a Guinea-Pig Lung-Vagus Preparation Ex Vivo The innervated guinea-pig lung preparation was prepared as was described in Undem B J, Chuaychoo B, Lee M G, Weinreich D, Myers A C, Kollarik M. Subtypes of vagal afferent C-fibres in guinea-pig lungs. *J Physiol* 2004; 556: 905-917; Weigand L A, Ford A P, Undem B J. A role for ATP in bronchoconstriction-induced activation of guinea pig vagal intrapulmonary C-fibres. *J Physiol* 2012; 590: 4109-4120. The contents of Undem et al. and Weigand et al. are incorporated herein for the purpose of the preparation of the innervated guinea-pig lung preparation. The response to ATP (10 μM; 1 ml, slowly infused into trachea and pulmonary artery) was assessed as the number of action potentials it elicited. Two control responses 15 minutes apart were recorded. There was not differences in the number of action potentials evoked between the first and second response (p>0.1). Subsequently, the lung superfused and perfused via both trachea and pulmonary artery for 15 min with increasing concentration of DT-0111 and the ATP challenge was repeated. The data were quantified as the total number of action potentials evoked and the peak frequency (Hz) as measured by the most action potentials evoked in any 1 s bin. DT-0111 was prepared in distilled water as a 10 mM solution, and aliquots were stored frozen at −20° C. (1-5 days).

Figure 5:
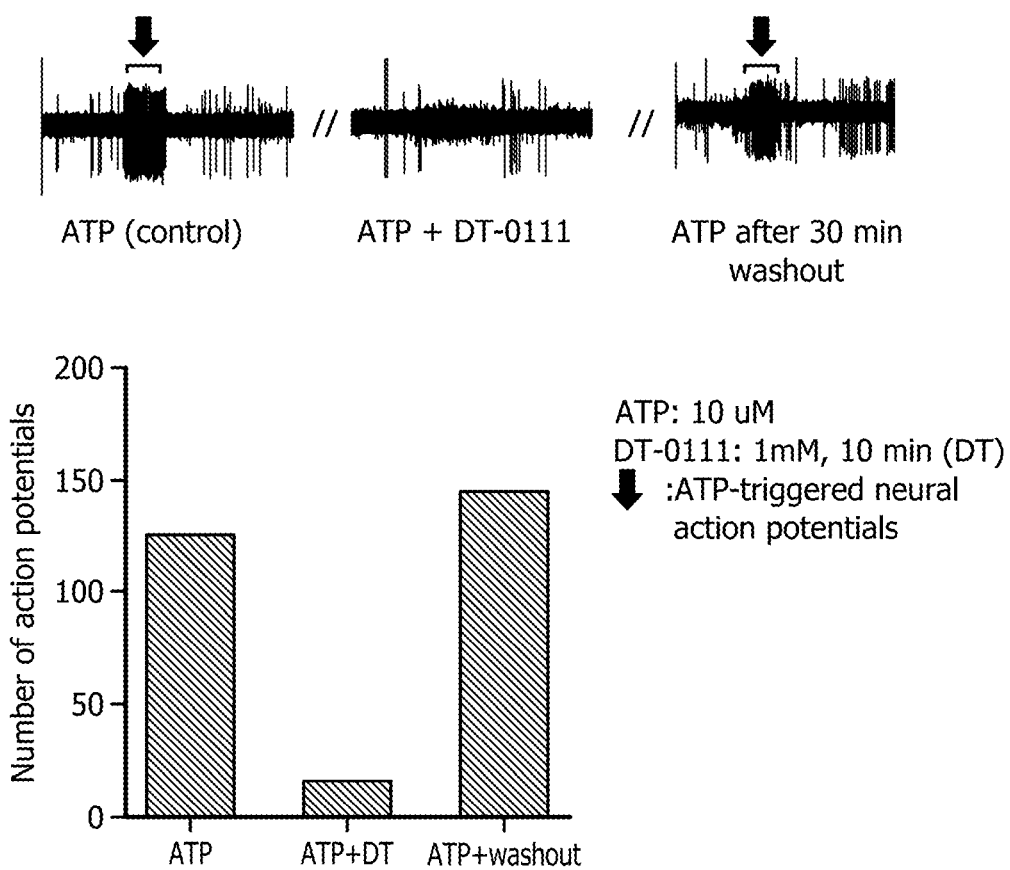
FIG. 5 shows a typical example of the effect of the Na salt of 3",5"-dimethoxybenzoyl-3'-amino-3'-deoxyadenosine-5'-triphosphate on ATP-induced neural action potential recordings in innervated guinea-pig lung ex vivo.

DT-0111 Blocks ATP-Induced Action Potentials in the Innervated Guinea-Pig Preparation Ex Vivo It has been demonstrated that DT-0111 antagonized the effect of ATP (10 μM) on nodose ganglion vagal sensory nerve terminals in the innervated guinea-pig-lung preparation ex vivo. In the upper portion of FIG. 5, a typical example of neural action potential (AP) recordings. At left, a burst of APs induced by ATP (control). In the middle, DT-0111 markedly suppresses the effect of ATP. At right, recovery of ATP's effect after 30 minutes of DT-11 washout. The lower portion of FIG. 5 shows the number of APs recorded in the absence (ATP), presence of DT-011 (1 mM) (ATP+DT), and after washout (ATP+washout). Arrows mark the administration of ATP.

Figure 6:
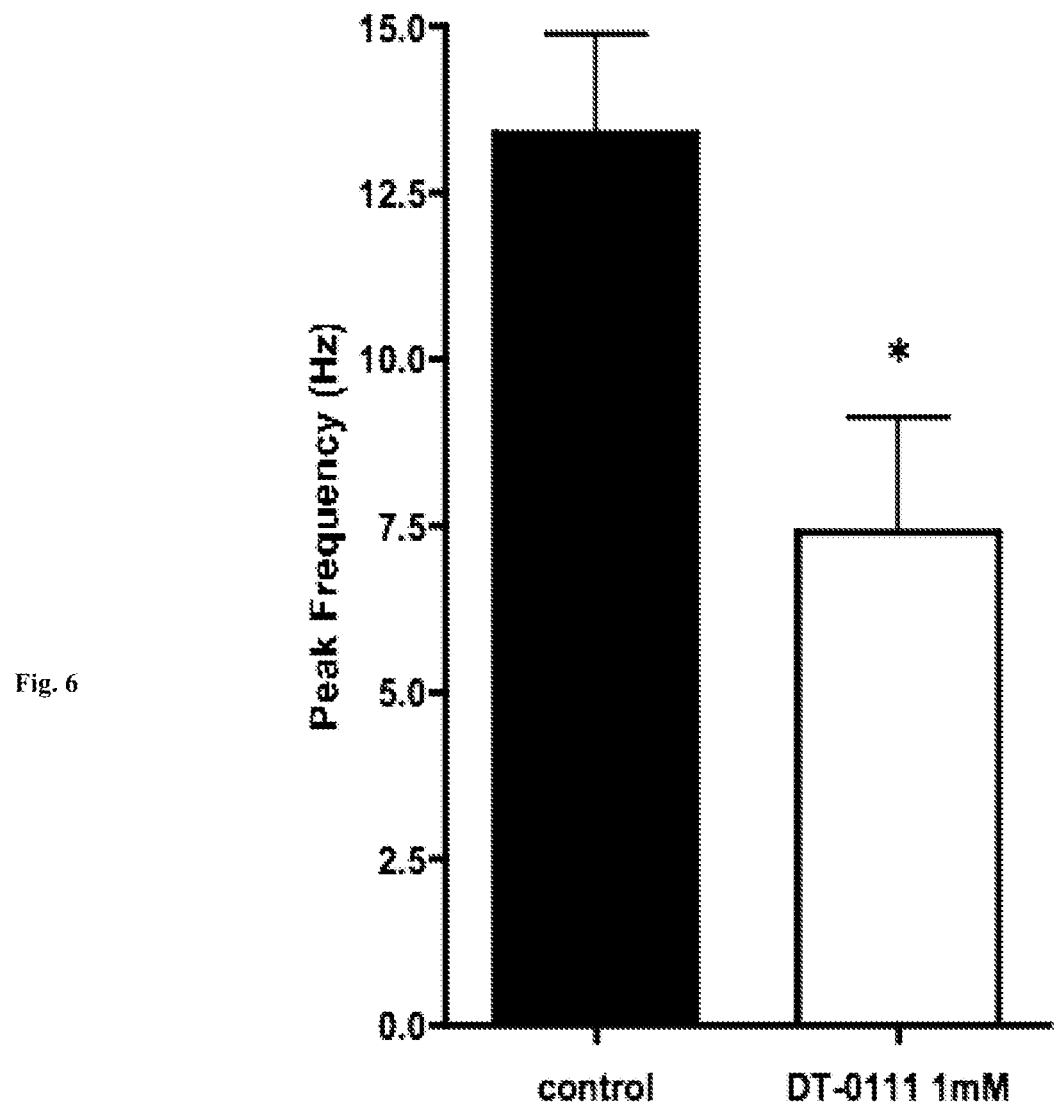
FIG. 6 shows peak action potential discharges in response to ATP in the absence and presence of the Na salt of 3",5"-dimethoxybenzoyl-3'-amino-3'-deoxyadenosine-5'-triphosphate.

FIG. 6 shows the peak action potential discharge (Hz) in response to ATP in the absence (black bar) and presence (white bar) of DT-0111 (1 mM). The data are presented as mean±SEM, n=10, * denotes p<0.05.

Example 4: Effect of DT-011 on ATP-Induced Bronchoconstriction in Anesthetized Guinea-Pig Male Dunkin-Hartley guinea pigs (GPs) (220-250 g, Charles River) were quarantined for 14 days. The housing room was constantly ventilated, and the temperature kept at 23° C. Mean body weight of the GPs on day of experiment was 336.0±9.9 g. Anesthesia were induced by using a mixture of ketamine+xylazine (40-80 mg/kg+5-10 mg/kg; IM) as previously published (Zhuang, et al., "High-Frequency Electrical Stimulatino of Cervical Vagi Reduces Airway Response to Methacholine," World J. of Respirology 2013 Jul. 28; 3(2): 11-19). Supplementary anesthetic doses (¼-½ of the original dose) were administered as needed if ear pinch changed respiratory rate and/or upon the manifestation of an accelerated heart rate. Body temperature was monitored continuously with a rectal thermometer and maintained at approximately 36.5° C. using a heating pad and lamp. The trachea was cannulated below the larynx and connected to a pneumotachograph to measure the airflow via a differential pressure transducer (ML141, AD Instruments, Castle Hill, Australia). Animals were exposed to a gas mixture of 30% oxygen in nitrogen throughout the experiment, and ventilated at a constant frequency ($f_R$) of 70-75 breaths/min with a tidal volume at 2.5 ml that was adjusted to keep end tidal pressure of $CO_2$ ($P_{ET}CO_2$) at 40 torr. Solutions of ATP (Sigma-Aldrich) used for aerosol challenge were freshly made just prior to use by dissolving the powder in 0.9% saline (NaCl) solution. DT-0111 solutions used for aerosol administration were freshly made by dissolving the powder in 0.9% saline (NaCl) solution. Saline and test solutions were aerosolized by a vibrating mesh nebulizer (Ireland Ltd., Galway Ireland, AG-AL1000) and directly delivered into the head chamber. The volume of the nebulizer's reservoir is ~10 ml. The output rate of delivered aerosol was 0.5 ml/min with an aerodynamic mass median diameter of 3.7 μm (manufacture's indications). The aerosol generated by the nebulizer was mixed with the airflow (1000 ml/min) to flow into a plastic cylinder (16 mm diameter). The latter was loosely jacketed the inspiration inlet (4.5 mm diameter) of the ventilator, by which the GP was ventilated with the aerosol delivered from the ventilator.

Estimated amount of DT-0111 inhaled into the airways and lungs: The aerosol exposure lasted two min during which 6 mg DT-0111 was mixed with 2000 ml airflow (1000 ml/min). The animal ventilation was 300 ml/2 min. Therefore, 6 mg×(300÷2000)=0.9 mg that is the approximate amount of DT-0111 inhaled into the airways and lungs during 2 min exposure. Based on the average body weight (336.0 g), the inhaled DT-011 was 2.6 mg/kg.

The side branch of the tracheal cannulation was connected a pressure transducer. The pressure signal was pre-amplified by a bridge amplifier (AD Instruments Inc., CO) and then digitized and recorded. The pressure signal was pre-calibrated with known water pressure (cm $H_2O$). The pressure signal and animal rectal temperature were monitored and digitally recorded continuously in computer files throughout the experiment using the PowerLab/8 sp data acquisition system (AD Instruments) with DELL XPS 8700 computer equipped with Microsoft Windows 7 and LabChart Pro 7 software.

After adequate anesthesia was established, the animal in supine position was placed in a standard chemical fume hood (size: 3×6 ft) where the ventilator and nebulizer were also located. After stabilization of signals (body temperature, airflow, and tracheal pressure) for 3-5 min (baseline conditions), the animal was exposed to a given dose of aerosolized ATP for 2 min. Following recovery, the animal was exposed to either another dose of ATP or the same dose of ATP ~10 min after inhalation of DT-0111 aerosol administered for 2 min. The interval between the first and second aerosol exposure was approximately 30-45 min.

Figure 7:
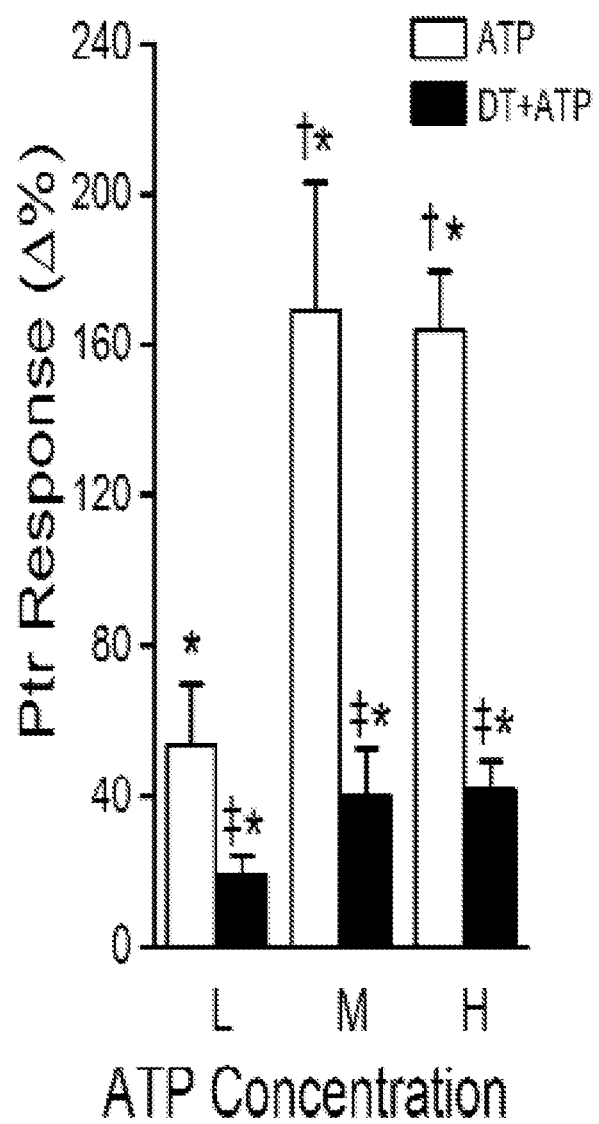
FIG. 7 shows results for the effect of the Na salt of 3",5"-dimethoxybenzoyl-3'-amino-3'-deoxyadenosine-5'-triphosphate on ATP-induced bronchoconstriction in anesthetized guinea-pigs.
Figure 8:
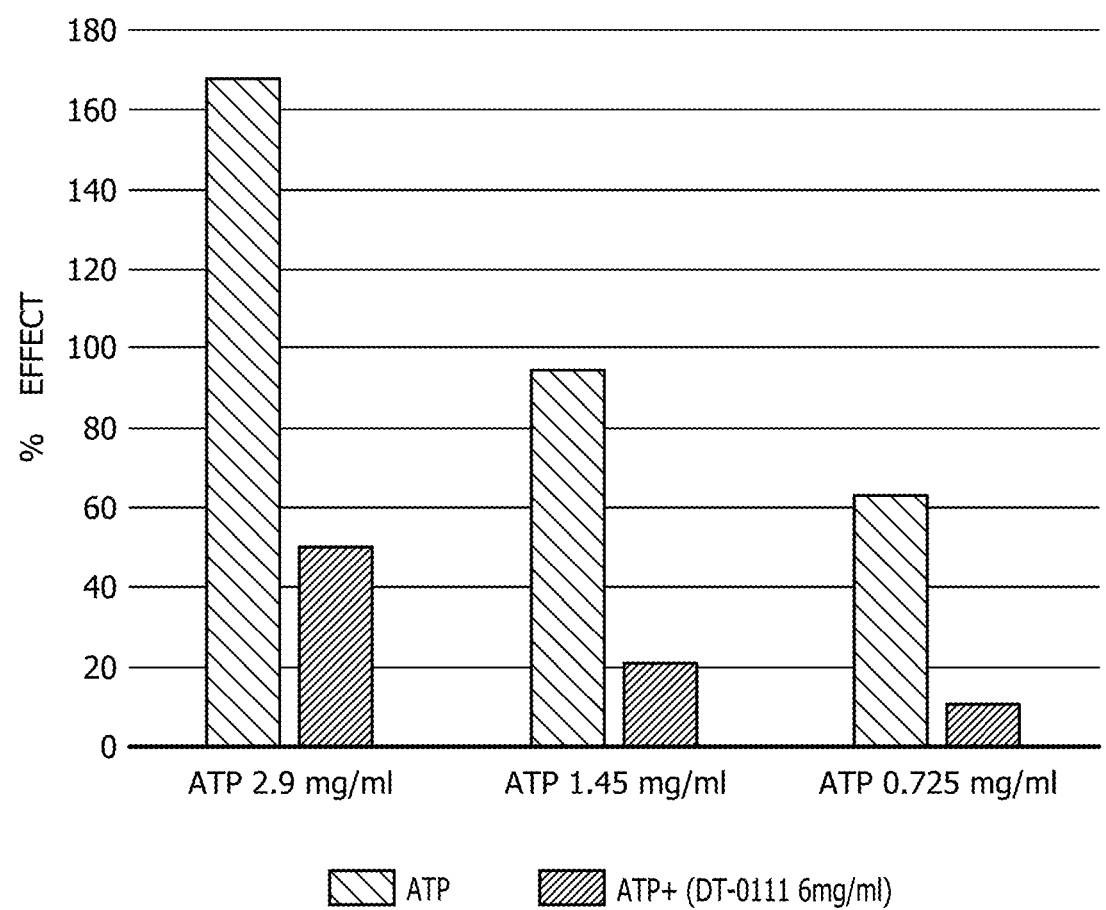
FIG. 8 shows a typical example of the inhibitory effect of aerosolized form of the Na salt of 3",5"-dimethoxybenzoyl-3'-amino-3'-deoxyadenosine-5'-triphosphate on aerosolized ATP-induced bronchoconstriction in the anesthetized guinea pig.

Tracheal pressure values were obtained 10 sec before (baseline, BL) and at the largest response value (peak)

during or after ATP exposure. The data was expressed either the absolute number and/or percent change from the baseline value (Δ%) (after vs. before aerosol inhalation). All group data were expressed as the means and compared before vs after aerosol. The results are presented in Table 1. It has been determined that tracheal pressure ($P_{tr}$) after ATP doses were significantly suppressed by pretreatment of aerosolized DT-0111. FIG. 7 shows results for doses L=low, M=middle, and H=high. $P_{tr}$ after medium and high doses were higher than those induced by low ATP dose. Data are mean±SE. *p<0.01, compared to baseline; p<0.01, compared to L ATP dose; and p<0.01, compared to before DT-0111 pre-treatment. FIG. 8 depicts a typical example of the inhibitory effect of aerosolized DT-0111 sodium salt on aerosolized ATP-induced bronchoconstriction in anesthetized guinea pig.

TABLE 1

Comparison of ATP effects in the same GPs before and after DT-0111 treatment

| GP ID | ATP Change (Δ%) | DT-0111 + ATP Change (Δ%) |
| --- | --- | --- |
| LC44565 | 64.3 | 10.8 |
| LC44566 | 113.2 | 12.9 |
| LC44566 | 16.4 | 11.2 |
| LC44567 | 169.3 | 50.2 |
| LC44567 | 93.9 | 20.1 |
| LC44567 | 62.4 | 10.0 |
| Mean | 86.6 | 19.2 |

Example 5: Aerosolized DT-01111 Suppresses Aerosolized ATP-Induced Broncho-Constriction and Cough (Demonstrated in Conscious Guinea-Pigs)

This study was performed in 6 guinea-pigs. The housing room was constantly ventilated, and the temperature kept at ~23° C. After quarantine, the animals were individually placed in a whole-body, unrestrained, plethysmograph chamber (model PLY3215, Buxco Electronics Inc., Troy, N.Y.) for ~40 min once a day for two continuous days before the cough test. All GPs were weighed before the cough study.

ATP was purchased from Sigma-Aldrich (Cat #A2383-10G). Solutions of ATP used for aerosol challenge were freshly made just prior to use by dissolving the powder in 0.9% saline (NaCl) solution. Solutions of DT-0111 used for aerosol administration were freshly made by dissolving the powder in 0.9% saline (NaCl) solution.

A plethysmograph chamber was continuously flushed with normoxic (21% $O_2$ and 79% $N_2$) room air at 2 L/min. The same amount of air was drawn through the chamber base outlets using a Buxco bias flow regulator to keep the chamber bias flow balanced. ATP or DT solution was aerosolized by using a vibrating mesh nebulizer (Ireland Ltd., Galway Ireland, AG-AL1100). The output rate of delivered aerosol was around 0.5 ml/min with droplet size (volume median diameter) at 2.5-4.0 μm (manufacture's indications). The aerosol was mixed with airflow and directly delivered into the plethysmograph chamber. The latter was placed in a standard chemical fume hood (size: 3×6 ft) installed in a standard laboratory.

A guinea-pig was placed in the chamber again after adaptation. Following stabilization, #1 guinea-pig was exposed to aerosolized ATP at 6 mg/ml, 24 mg/ml, and then 48 mg/ml for 5 min with an interval of 30 min. The remaining animals (#2-#6 guinea-pigs) were exposed to aerosolized ATP at 48 mg/ml for 5 min. Approximately 140 min later, the same dose of ATP was repeated immediately after DT-0111 aerosol inhalation (12 mg/ml for 5 min). Choose of DT-0111 dose is based on the results from Study 3 in which it significantly blunted the ATP-induced bronchoconstriction. The cough sound and behavioral activities were continuously monitored and recorded before (for 3 min), during 5 min aerosol delivery, and 20 min after cessation of the delivery.

Setup of the cough recording system. The top of the plethysmograph chamber was connected with a plastic tube that was attached by the nebulizer. Normoxic air driven by the nebulizer controller was flowed into the chamber and sucked out by the bias flow regulator with the in and out flow volume balanced (2.0 L/min). To detect cough, a microphone system was mounted in the roof of the chamber to record sound; a video camera was placed outside of the chamber to monitor animal body posture; and a Buxco pneumotachograph (differential pressure transducer) attached to the chamber to record airflow. All signals generated by video camera, microphone, and pressure transducer were amplified and recorded continuously by PowerLab/8 sp (model ML 785; ADInstruments Inc., Colorado Springs, Colo.) and a computer with the LabChart Pro 7 software.

Cough count. A typical cough response, as reported before (Girard et al., Eur Respir J, 1995; Blasko et al., American Journal of Advanced Drug Delivery. 5:131-138, 2017; Corboz et al., Journal of Pharmacology and Experimental Therapeutics. 363: 348-357, 2017), was defined by the simultaneous appearance of: 1) a transient and great change in the airflow (a rapid inspiration followed by rapid expiration); 2) a typical cough sound with the peak power density at 1-2 kHz in frequency spectrum (sneeze at 3.5-6.5 kHz); and 3) animal body (head) posture and movement.

Figure 9:
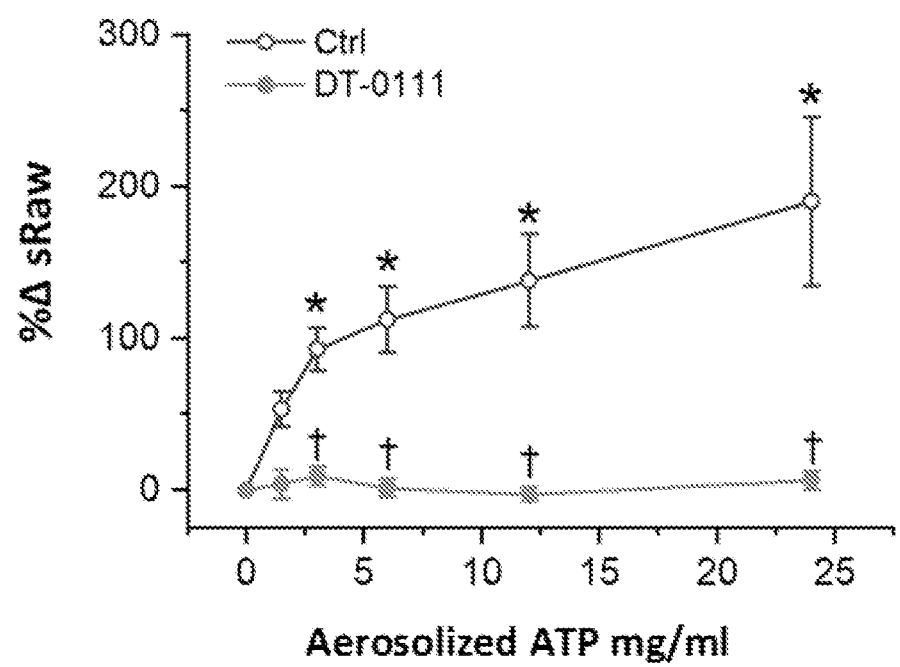
FIG. 9 shows the bronchoconstrictive effect of inhaling increasing doses of aerosolized ATP before and after an aerosolized form of the Na salt of 3",5"-dimethoxybenzoyl-3'-amino-3'-deoxyadenosine-5'-triphosphate in conscious guinea-pigs.

FIG. 9 shows the bronchoconstrictive effect of inhaling increasing doses of aerosolized ATP before (control, labelled "Ctrl") and after aerosolized DT-0111 in conscious guinea-pigs. The results are expressed as percent change in airway pressure (sRaw). n=6; * p<0.05, vs. ATP 0.0 mg/ml; †p<0.05, DT-0111 vs. Ctrl at the same ATP dose.

Figure 11:
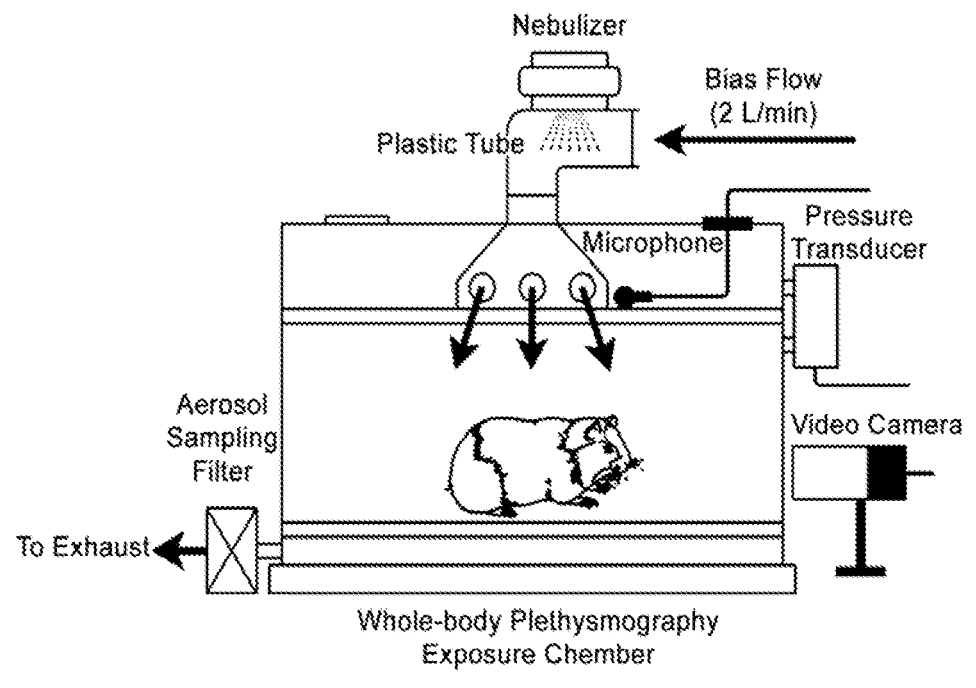

FIG. 11 shows the utilized exposure chamber and setup of cough recording system. Arrows point to the flow direction. The signals generated by video camera, microphone, and pressure transducer were amplified, digitized, and recorded continuously through a PowerLab system and LabChart Pro software (ADInstruments). In all animals (guinea-pigs (GP)), aerosolized ATP at 48 mg/ml for 5 min exposure evoked significant coughs. The coughs are characterized by mixture of bout(s) of coughs and individual coughs (Table 2). Four of six GPs tested presented 2 bouts and the remaining two showed one bout of coughs. In these cases, the individual coughs (1-3 coughs) occurred after the bout of coughs with louder cough sound compared to the bout of coughs. In the remaining two of six GPs, the individual coughs without bout(s) of cough were observed.

TABLE 2

Effects of DT aerosol inhalation on ATP aerosol exposure-induced cough response

| GP_ID | BW (g) | ATP (48 mg/ml) | | | | DT (12 mg/ml) + ATP (48 mg/ml) | | | |
|---|---|---|---|---|---|---|---|---|---|
| | | Bout Cough | | Individual | | Bout Cough | | Individual | |
| | | $B_1$# | $B_2$# | Cough | Subtotal | $T_1$# | $T_2$# | Cough | Subtotal |
| 54270 | 324 | 21 | 0 | 1 | 22 | NA | NA | NA | NA |
| 53145 | 322 | 21 | 0 | 1 | 22 | 0 | 0 | 7 | 7 |
| 53146 | 365 | 24 | 0 | 3 | 27 | 0 | 0 | 0 | 0 |
| 54271 | 388 | 14 | 10 | 0 | 24 | 0 | 0 | 1 | 1 |
| 55017 | 349 | 18 | 16 | 1 | 35 | 0 | 0 | 1 | 1 |
| 55018 | 348 | 19 | 0 | 0 | 19 | 0 | 0 | 0 | 0 |
| Mean | 354 | | | | 25.4 | | | | 1.8 |
| SE | 11 | | | | 2.7 | | | | 1.3 |

Note:
DT-0111 was not tested in animal #54270. $B_1$# and $B_2$# are the cough numbers in the first and second bout of cough.

Figure 10:
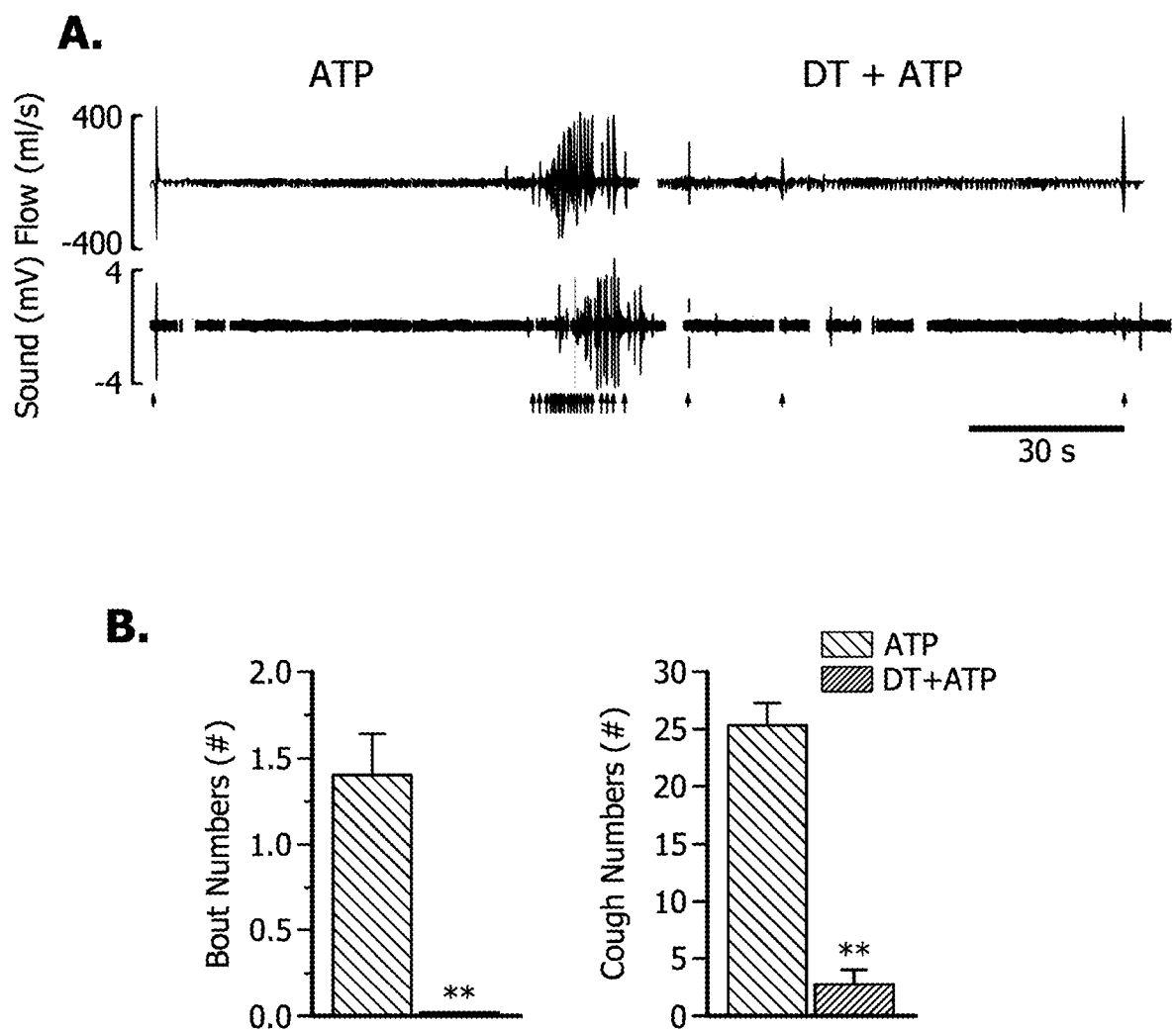
FIG. 10 shows the effects of an aerosolized form of the Na salt of 3",5"-dimethoxybenzoyl-3'-amino-3'-deoxyadenosine-5'-triphosphate on aerosolized ATP-induced cough in conscious free moving guinea-pigs.

Aerosolized DT-0111 (12 mg/ml) blocked the bout of coughs in all tested animals (n=5) with varied effect on the individual coughs, i.e., no change, elevation, and decrease in 2, 2, and 1 GPs, respectively (Table 2). The typical recordings of cough responses before and after DT-0111 and the corresponding group data are illustrated in FIG. 10(A) and FIG. 10(B), respectively. Statistically, DT-0111 eliminated the bout of coughs with little effect on individual coughs. DT-0111 per se did not evoke any cough.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

The invention claimed is:

1. A compound according to Formula (I), or a pharmaceutically acceptable salt thereof:

wherein:
$R^1$ and $R^2$ are independently selected from $(C_1-C_6)$ alkyl.

2. The compound according to claim 1 wherein $R^1$ and $R^2$ are methyl, or a pharmaceutically acceptable salt thereof.

3. The compound according to claim 1, wherein the compound is a sodium salt of the following formula:

4. A pharmaceutical composition comprising a pharmaceutically acceptable carrier and a compound according to claim 1, or pharmaceutically acceptable salt prodrug thereof.

5. A method of treating respiratory disease in which extracellular ATP plays a mechanistic role comprising administering to the subject in need of such treatment a therapeutically effective amount of a compound according to claim 1, or pharmaceutically acceptable salt thereof.

6. The method according to claim 5 wherein the respiratory disease is a cough related respiratory disease.

7. The method according to claim 6 wherein cough-related the respiratory disease is chronic obstructive pulmonary disorder (COPD), bronchospasm or asthma.

8. The method according to claim 5 wherein the respiratory disease is disease is sub-acute cough, chronic cough, treatment-resistant cough, idiopathic chronic cough, cough associated with upper respiratory infection, post-viral cough, iatrogenic cough, idiopathic pulmonary fibrosis or cough associated with smoking or a form of bronchitis.

9. The method according to claim 5, wherein $R^1$ and $R^2$ are methyl in the compound of Formula (I), or in the pharmaceutically acceptable salt thereof.

10. A method of treating bladder overactivity or urinary incontinence comprising administering to a subject in need of such treatment a therapeutically effective amount of a compound according to claim 1, or pharmaceutically acceptable salt thereof.

11. The method according to claim 10 wherein the bladder overactivity comprises one or more of urinary urgency, urinary frequency, altered bladder capacity, micturition threshold, unstable bladder contractions, sphincteric spasticity, detrusor hyperreflexia and detrusor instability.

12. The method according to claim 10 where in the disorder of the bladder is interstitial cystitis.

13. The method according to claim 10, wherein $R^1$ and $R^2$ are methyl in the compound of Formula (I), or in the pharmaceutically acceptable salt thereof.

14. A method of treating pain comprising administering to a subject in need of such treatment a therapeutically effective amount of a compound according to claim 1, or pharmaceutically acceptable salt thereof.

15. The method according to claim 14 wherein the pain is nociceptive pain.

16. The method according to claim 14 wherein the pain is neuropathic pain.

17. The method according to claim 14, wherein $R^1$ and $R^2$ are methyl in the compound of Formula (I), or in the pharmaceutically acceptable salt thereof.

18. A process for preparing a compound according to Formula (I),

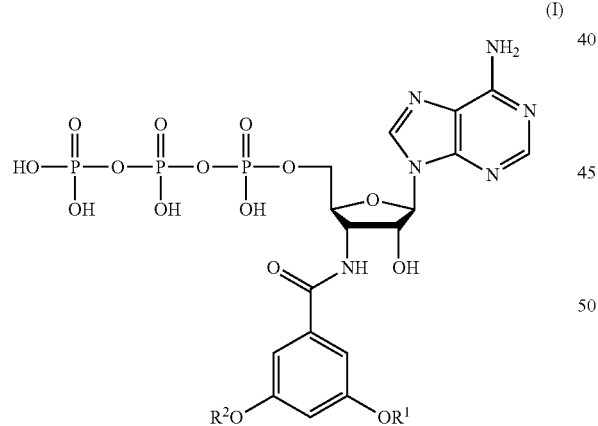

wherein:
$R^1$ and $R^2$ are independently selected from $(C_1$-$C_6)$ alkyl;
the process comprising:
(a) reacting the compound 1

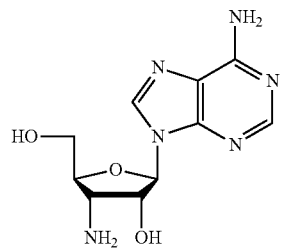

with a compound of Formula (IIa)

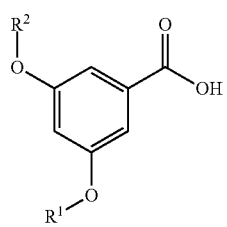

to form a compound according to Formula (III);

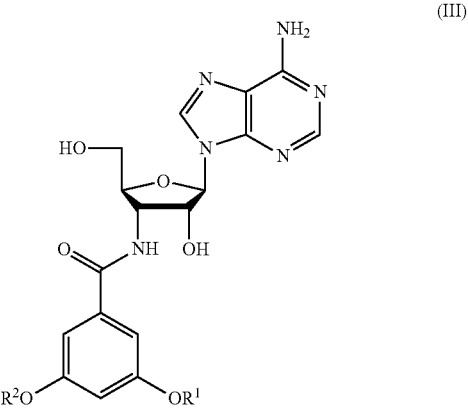

(b) 5'-phosphorylating the compound according to Formula (III) to provide a compound according to Formula (I).

19. The process according to claim 18 wherein $R^1$ and $R^2$ are methyl.

* * * * *

UNITED STATES PATENT AND TRADEMARK OFFICE
CERTIFICATE OF CORRECTION

| | | |
|---|---|---|
| PATENT NO. | : 11,440,935 B2 | Page 1 of 1 |
| APPLICATION NO. | : 16/981242 | |
| DATED | : September 13, 2022 | |
| INVENTOR(S) | : Amir Pelleg et al. | |

It is certified that error appears in the above-identified patent and that said Letters Patent is hereby corrected as shown below:

On the Title Page

Assignee item (73) Line 1 delete "MERCK PATENT GMBH" and insert -- DANMIR THERAPEUTICS, LLC --

Signed and Sealed this
Twenty-first Day of March, 2023

Katherine Kelly Vidal
*Director of the United States Patent and Trademark Office*